United States Patent
Hayakawa

(10) Patent No.: US 9,877,762 B2
(45) Date of Patent: Jan. 30, 2018

(54) BONE TREATMENT SYSTEM

(71) Applicant: TERUMO KABUSHIKI KAISHA, Shibuya-ku (JP)

(72) Inventor: Koichi Hayakawa, Machida (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 630 days.

(21) Appl. No.: 14/488,450

(22) Filed: Sep. 17, 2014

(65) Prior Publication Data
US 2015/0094730 A1  Apr. 2, 2015

(30) Foreign Application Priority Data
Sep. 27, 2013  (JP) .................................. 2013-202730

(51) Int. Cl.
*A61B 17/88* (2006.01)
*A61B 17/70* (2006.01)

(52) U.S. Cl.
CPC ...... *A61B 17/8811* (2013.01); *A61B 17/7097* (2013.01); *A61B 17/8855* (2013.01)

(58) Field of Classification Search
CPC .................... A61B 17/8855; A61B 17/8811
See application file for complete search history.

(56) References Cited

U.S. PATENT DOCUMENTS

| | | | |
|---|---|---|---|
| 6,932,843 B2* | 8/2005 | Smith ............... | A61B 17/8811 623/17.11 |
| 7,144,398 B2* | 12/2006 | Chern Lin ......... | A61B 17/7097 606/92 |
| 2004/0059417 A1 | 3/2004 | Smith et al. | |
| 2005/0209595 A1 | 9/2005 | Karmon | |
| 2005/0216025 A1 | 9/2005 | Chern Lin et al. | |
| 2008/0300604 A1 | 12/2008 | Lu et al. | |
| 2013/0226296 A1 | 8/2013 | Chernomorsky et al. | |

FOREIGN PATENT DOCUMENTS

| | | |
|---|---|---|
| JP | 2006-505339 A | 2/2006 |
| WO | WO 2004/043303 A2 | 5/2004 |
| WO | 2007/134374 A1 | 11/2007 |

OTHER PUBLICATIONS

European Search Report dated Jan. 29, 2015, by the European Patent Office in corresponding European Application No. 14181863.3-1506. (7 pages).

* cited by examiner

*Primary Examiner* — Andrew Yang
(74) *Attorney, Agent, or Firm* — Buchanan Ingersoll & Rooney PC

(57) ABSTRACT

To easily and accurately place a bone filling material in a cured state at a bone treatment target, a bone treatment system includes a placement device and a deployment operation device. The placement device includes a shaft having a flow path which enables a bone filling material to be placed on a space of a radius to flow therethrough, and a filling balloon to be filled with the bone filling material via the flow path 38 disposed in a distal end portion of the shaft. The deployment operation device 16 can be inserted into the flow path, and exposes the bone filling material by breaking the filling balloon after being filled with the bone filling material.

19 Claims, 16 Drawing Sheets

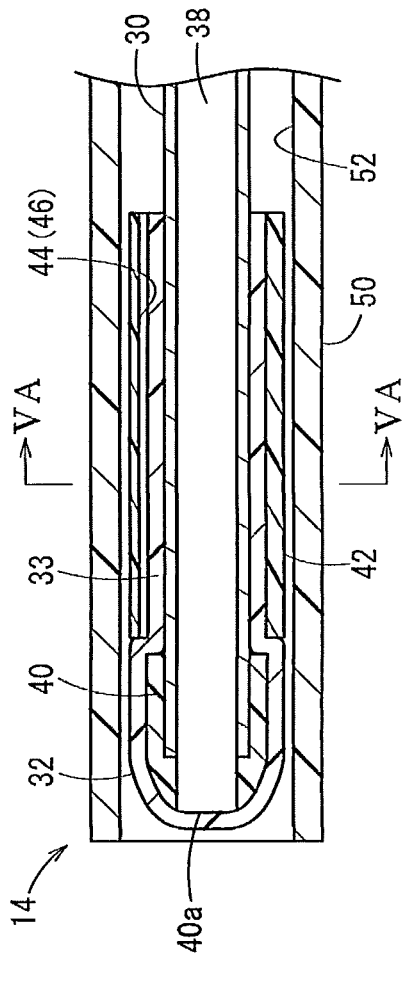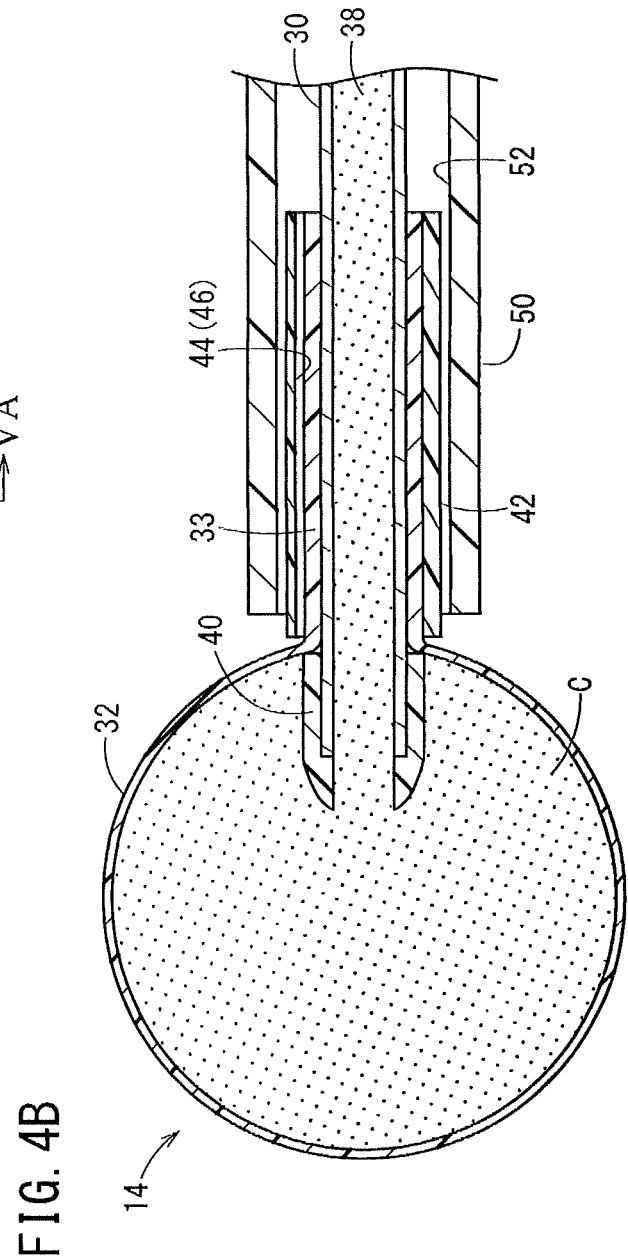

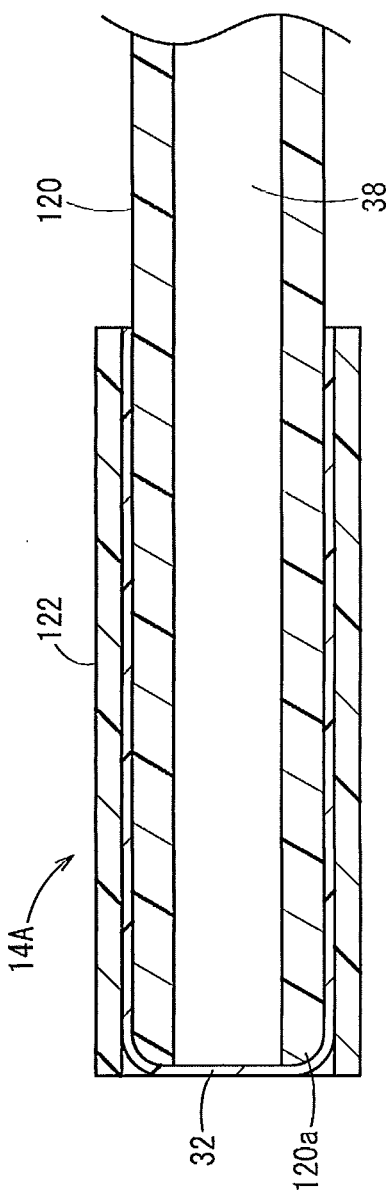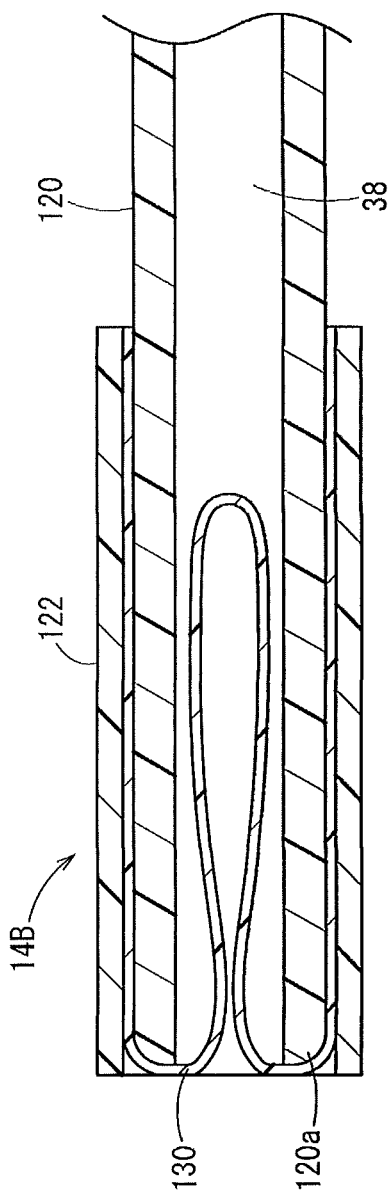

BONE TREATMENT SYSTEM

CROSS-REFERENCES TO RELATED APPLICATIONS

This application claims priority to Japanese Application No. 2013-202730 filed on Sep. 27, 2013, the entire content of which is incorporated herein by reference.

TECHNICAL FIELD

The present invention generally relates to a bone treatment system for placing a bone filling material on a bone treatment site.

BACKGROUND DISCUSSION

If a person has, for example, osteoporosis due to rarefied bone density, in some cases, he or she may suffer a wrist fracture (distal radius fracture) by putting his or her hand on something when falling down. Currently, treatment for the distal radius fracture has adopted a plate fixing technique in which a plate (mainly a locking plate) is arranged so as to cross from a fractured main bone piece to a peripheral bone piece, and the plate and each bone are repositioned and fixed by a screw. However, since the plate is installed outside the bone, there is a possibility that the screw or an end portion of the plate may damage surrounding tissues (flexor tendon, extensor tendon, or the like). In addition, there are some medical cases in which it is necessary to remove the screw from the plate in order to avoid complications such as tendon rupture and the like. In this case, it is necessary to carry out surgery by incising the skin twice, when the plate is installed and when the screw is removed.

Therefore, in the treatment for the bone fracture, treatment which is less invasive and has fewer complications is required. For example, as disclosed in Japanese Application Publication No. 2006-505339 (JP-T-2006-505339), a method is proposed in which a bone filling material is placed inside the bones so as to promote osteosynthesis. A device disclosed in Japanese Application Publication No. 2006-505339 Japanese Application Publication No. 2006-505339 includes a balloon configured to have a bioabsorbable material in a distal end portion of the device. During the treatment, the balloon filled with the bone filling material is placed inside the bone. If the balloon is absorbed into a living body after the placement, the bone filling material cured inside the balloon is exposed, and supports a bone fracture site from the inside of the bone instead of the plate or the screw in the previously described plate fixing technique. In this manner, the osteosynthesis is promoted.

SUMMARY

In the treatment disclosed in Japanese Application Publication No. 2006-505339, the balloon formed of the bioabsorbable material is placed in a state of being filled with the bone filling material. Consequently, a treatment period is considerably lengthened since the bone filling material needs a lot of time to show effectiveness. That is, it is desirable to initially expose the bone filling material from the balloon and to place the bone filling material inside the bone.

However, in a case of the bone filling material which is very hydrophilic, if the bone filling material is exposed from the balloon in a state of having fluidity prior to curing (state of liquid or paste), the bone filling material is relatively easily disintegrated and dispersed in a body. Consequently, the osteosynthesis becomes difficult. Therefore, in the treatment using the bone filling material, it is necessary to cure the bone filling material to a placement-available degree after filling the balloon. However, in this case, it is difficult to place a larger and cured bone filling material that can be exposed from the balloon inside the bone.

The bone treatment system disclosed here can more favorably treat the bone by easily placing the cured bone filling material for a bone treatment target.

The bone treatment system disclosed here includes a shaft possessing a lumen configured to permit a bone filling material to flow through the lumen and be delivered to a bone treatment site; a balloon disposed on a distal end of the shaft configure to be filled with the bone filling material via the lumen; and a deployment operation device insertable into the lumen and configured to break the balloon after the balloon is in an inflated state filled with the bone filling material to expose the bone filling material.

Since the bone treatment system includes the balloon and the deployment operation device, it is possible to rather easily place the bone filling material in a cured state on a bone treatment site. That is, in the bone treatment, the balloon is arranged in the bone treatment site, the inside of the balloon is filled with the bone filling material, and the deployment operation device is inserted into the lumen before the bone filling material is cured. In this manner, when the bone filling material is cured, a hollow portion is formed inside the bone filling material, and thus it is possible to carry out work in which the deployment operation device breaks the balloon via this hollow portion. As a result, the bone filling material in the cured state is easily exposed from the balloon and is placed on the bone treatment side. Accordingly, it is possible to more favorably treat the bone. In particular, the bone filling material which is easily disintegrated or poorly cured if the bone filling material comes into contact with a body fluid when injected can be placed inside the bone in a state where influence of the body fluid is suppressed and the bone filling material is more reliably cured. Therefore, it is possible to improve strength of a fracture site and to increase a treatment effect.

In this case, it is preferable that the balloon be made of an elastic material.

In this manner, since the balloon has elasticity, it is possible to relatively easily insert the balloon in a deflated state into the bone. In addition, when the operation is completed in which the balloon is in the inflated state and is broken by the deployment operation device, it is possible to rather easily collect the balloon from the inside of the bone by moving the broken balloon to the shaft side so that the balloon is deflated.

In addition, the deployment operation device may include an insertion member which is insertable into the lumen and the balloon, and whose distal end portion is movable close to or into contact with an inner surface of the balloon in an inflated state.

Therefore, it is possible to cure the bone filling material in a state where the insertion member is inserted after filling the bone filling material. As a result, it is possible to rather easily form the hollow portion communicating with the balloon in the cured bone filling material. Accordingly, it is possible to rather easily perform a deployment operation with respect to the balloon by utilizing this hollow portion.

In addition, it is preferable that the deployment operation device further include a needle member which is guided inside a hollow portion formed as the insertion member is pulled out from the bone filling material, and which breaks the balloon.

In this manner, when the bone filling material in the cured state is deployed into the bone, the needle member can relatively easily break the balloon, and the bone filling material can be smoothly exposed.

Alternatively, the deployment operation device may be configured to cause a solution for dissolving the balloon to flow into a hollow portion formed as the insertion member is pulled out from the bone filling material, thereby breaking the balloon.

This allows the balloon to be broken rather easily and the bone filling material can be smoothly exposed even with the solution flowing into the hollow portion.

In addition, the insertion member may be a tubular body having a penetrating path in an axial direction, and the deployment operation device may further include a needle member which is inserted into the penetrating path and breaks the balloon.

In this manner, the insertion member has the penetrating path, and the needle member inserted into the penetrating path breaks the balloon. Accordingly, it is possible to break the balloon in a state where the insertion member is inserted into the cured bone filling material. Therefore, it is possible to more quickly expose the bone filling material.

Furthermore, it is preferable that the balloon in an inflated state be configured so that a thickness of a portion which a distal end portion of the insertion member comes into contact with or moves close to is thinner than a thickness of the vicinity of an attachment portion between the balloon and the shaft.

The balloon is thus formed so that the thickness of the portion which comes into contact with or moves close to the hollow portion is thinner. Accordingly, it is possible to easily break the balloon when the bone filling material is exposed from the balloon by the deployment operation device. The balloon after being ruptured excellently moves to the attachment position side of the shaft in which the thickness is thick. Accordingly, it is possible to easily collect the balloon.

Furthermore, it is preferable that an outer peripheral surface of the insertion member be coated with lubricant for the insertion member having a lubricating property for the cured bone filling material.

The outer peripheral surface of the insertion member is coated with the lubricant for the insertion member. Accordingly, it is possible to easily pull out the insertion member from the cured bone filling material.

Furthermore, the balloon may have an imaging unit which can recognize the balloon during radiation (X-ray) photography.

In this manner, since the balloon has the imaging unit, it is possible to easily recognize an inflated state of the balloon, rupture of the balloon.

The bone treatment system disclosed here makes it possible to more favorably treat a bone by rather easily placing a cured bone filling material on a bone treatment target.

According to another aspect, a bone treatment system comprises: a shaft possessing a distal end portion at which is held a balloon possessing an interior that is fillable with bone filling material, with the balloon being inflatable in a distal direction of the shaft so that the inflated balloon extends distally beyond a distal-most end of the shaft, and with the distal end of the shaft including the balloon being configured to be positioned in a space spanning a fracture in a bone. The shaft includes a lumen extending along the shaft, with the lumen in the shaft communicating with both an injection port which is connectable to a bone filling material source and the interior of the balloon so that when the bone filling material source is connected to the injection port, bone filling material is conveyed along the lumen and introduced into the interior of the balloon while the balloon is positioned in the space spanning the fracture to fill the balloon and cause the balloon to inflate in the space. The system also includes an elongated mandrel configured to be introduced into the lumen while the balloon filled with the bone filling material is positioned in the space so that the elongated mandrel passes through the bone filling material, and to be removed from the bone filling material after curing of the bone filling material to produce a passage in the bone filling material that communicates with the balloon. Also, a needle member is configured to be introduced into the lumen after the elongated mandrel is removed and while the balloon filled with the cured bone filling material and provided with the passage is positioned in the space to move a tip end of the needle into contact with the balloon to break the balloon so that the balloon is removable from the space together with the shaft while the cured bone filling material remains in the space.

In accordance with another aspect, a method of treating a fracture in a bone, comprising: inserting a balloon into a space in the bone, the space spanning the fracture in the bone, the balloon possessing an interior; introducing bone filling material into the interior of the balloon to inflate the balloon in the space to and cause the balloon to contact the bone surrounding the space; breaking the balloon to expose the bone filling material in the space; and removing the balloon from the space while the bone filling material remains in the space.

BRIEF DESCRIPTION OF DRAWINGS

FIG. 4A is a partial cross-sectional view illustrating an enlarged distal end portion of the placement device in FIG. 3, and FIG. 4B is a partial cross-sectional view illustrating an inflated state of a filling balloon of the placement device in FIG. 3.

FIG. 10A is a side cross-sectional view illustrating a placement device according to a first modification example, and FIG. 10B is a side cross-sectional view illustrating a placement device according to a second modification example.

DETAILED DESCRIPTION

Hereinafter, embodiments of a bone treatment system representing examples of the bone treatment system disclosed here will be described in detail with reference to the accompanying drawings.

Figure 1:
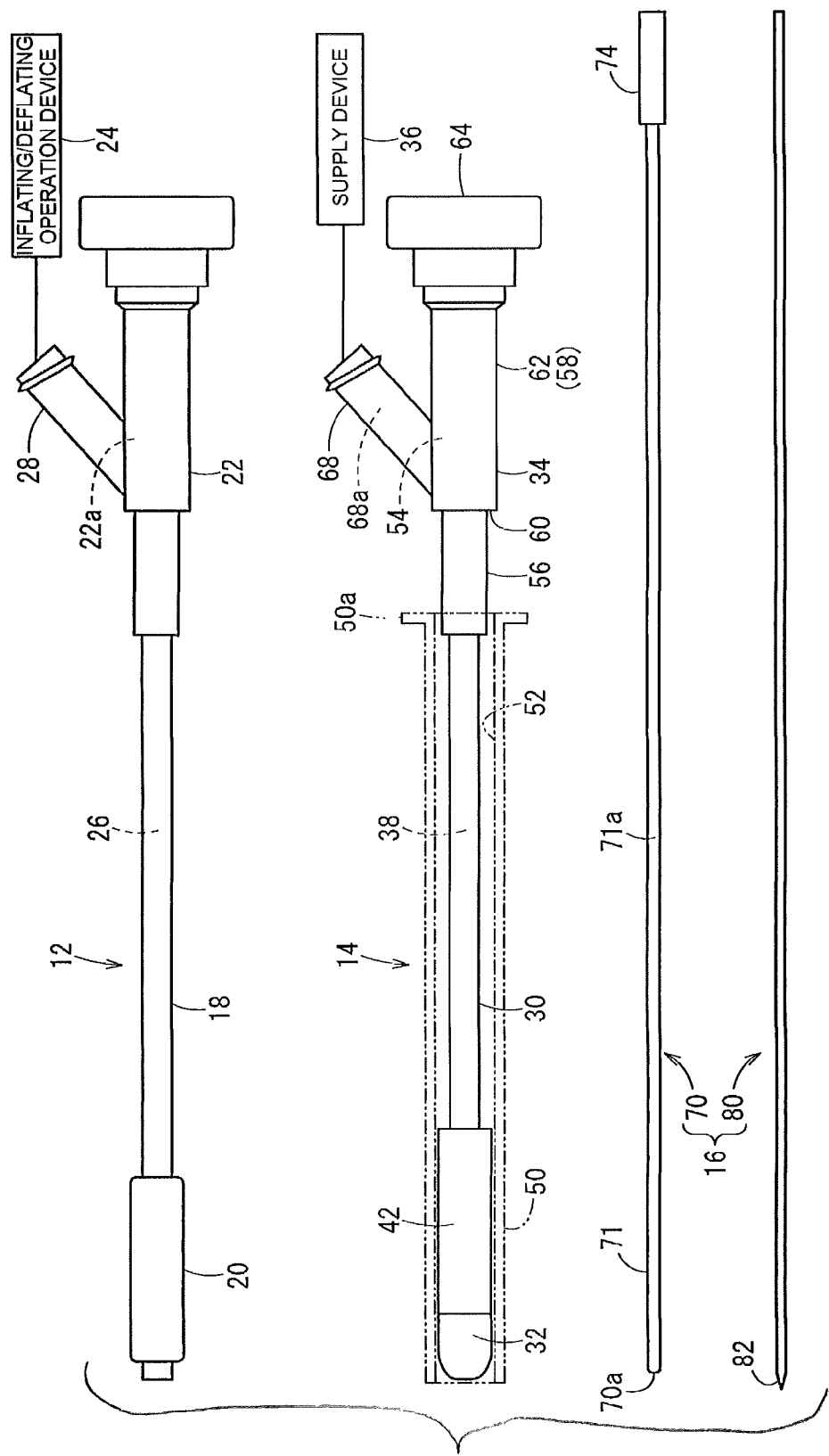
FIG. 1 is a side view illustrating an overall configuration of a bone treatment system representing one example of the bone treatment system disclosed here.
Figure 2:
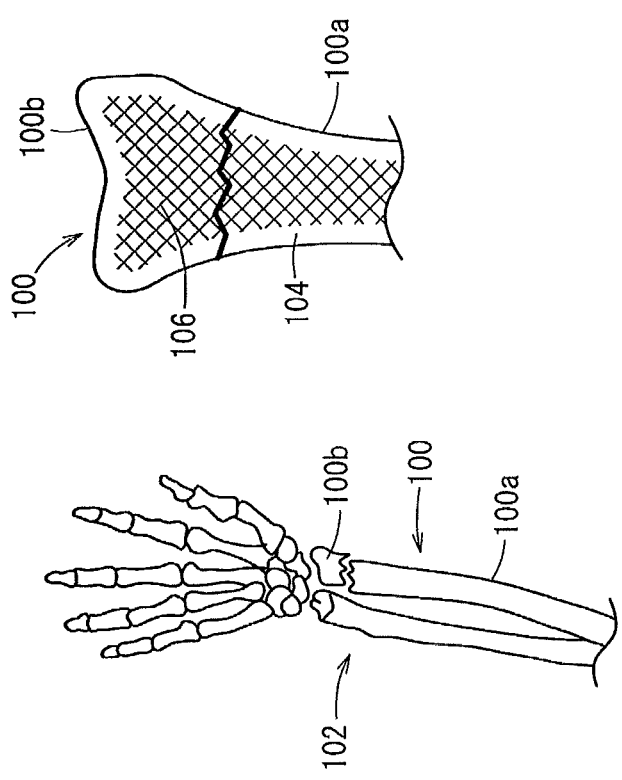
FIG. 2A is a schematic view illustrating a distal radius fracture to which the bone treatment system in FIG. 1 is applied.
FIG. 2B is a first illustrating view for illustrating flow of treatment for the distal radius fracture in FIG. 2A.
FIG. 2C is a second illustrating view for illustrating flow of the treatment subsequent to FIG. 2B.
FIG. 2D is a third illustrating view for illustrating flow of the treatment subsequent to FIG. 2C.

A bone treatment system 10 is a system in which multiple devices illustrated in FIG. 1 perform low invasive treatment on a patient's fracture site by using a bone filling material C (placement material shown in FIG. 2C). That is, a surgeon manually operates the device for placing the bone filling material C inside a bone by using the multiple devices of the bone treatment system 10 at a predetermined timing. The placed bone filling material C treats the bone with the lapse of time.

The "bone filling material" described here refers to those materials which can fill a bone treatment site in an initial stage (for example, liquid or paste) and are cured (for example, solidified or semi-solidified) with the lapse of time. Then, the "bone filling material" is a material which enables bone treatment (also including bone ameliorating such as osteosynthesis promotion and augmentation, in addition to osteosynthesis) to be performed on the bone at which the material is placed by way of fusion, absorption, substitution, organization, or the like.

A material for this bone filling material C is not particularly limited, but for example, it is possible to preferably use a polymethacrylate resin (PMMA) such as polymethyl methacrylate, α-type tricalcium phosphate (TCP), p-type TCP, and calcium phosphate cement (CPC) such as hydroxyapatite. In particular, the CPC is preferably used since the CPC enables the osteosynthesis by being solidified from paste within a relatively short time, being gradually joined to (absorbed in) the bone from a solidified state, and being eventually substituted with an autologous bone. The bone filling material C includes so-called "bone cement". The bone cement represents the above-described PMMA in a narrow sense, but includes the PMMA and the CPC in a broad sense.

For example, a treatment target (site) using the bone treatment system 10 includes a wrist fracture (distal radius fracture). As a matter of course, this bone treatment system 10 is not limited to the treatment for the distal radius fracture, and can be applied to treatment for other bone fracture sites or bone augmentation for osteoporosis. In addition, the treatment site is not limited to the inside of the bone, and the bone treatment system 10 can target various positions where the bone filling material C can be placed. Furthermore, the bone treatment system 10 can be applied to the bone treatment for animals in addition to humans, of course.

In the following description, when indicating or referring to directions of the respective devices of the bone treatment system 10, the left side in FIG. 1 is referred to as a "distal" side, and the right side in FIG. 1 is referred to as a "proximal" side.

To facilitate an understanding of the bone treatment system 10 according disclosed here, an overview of the treatment for the distal radius fracture using the placement of the bone filling material C will be first described. As illustrated in FIG. 2A, a human body has a radius 100 located near a thumb and an ulna 102 located near a little finger, as bones of an upper limb on a further distal side than an elbow. The radius 100 includes a body portion 100a, a distal end portion 100b and a proximal end portion which are located at both ends of the body portion 100a and are thicker than the body portion 100a. The osteoporosis of the radius 100 represents a state where bone tissues of a trabecular bone 106 on an inner side are lost as compared to a compact bone 104 on an outer peripheral surface side of the bone and thus bone density is rarefied.

The distal radius fracture occurs since the compact bone 104 in a connection portion between the body portion 100a and the distal end portion 100b receives a shock and is destroyed (divided or cracked). A specific fracture state includes a closed fracture in which the divided distal end portion 100b is misaligned with the body portion 100a (also including Colles' fracture), an opened fracture, or an impression fracture in which the body portion 100a is forced into the distal end portion 100b.

As illustrated in FIG. 2B, in the treatment for the distal radius fracture, repositioning work is carried out in order to restore a position of the distal end portion 100b which is misaligned with the body portion 100a. This allows the body portion 100a and the distal end portion 100b to be mutually arranged at a normal position (hereinafter, referred to as a repositioned state).

In this repositioned state, positions of the body portion 100a and the distal end portion 100b are maintained, and as illustrated in FIG. 2C, a placement measure of the bone filling material C is executed using the bone treatment system 10. Although this placement measure will be described later, in a schematic configuration, the bone treatment system 10 forms a space 108 (at a position spanning the fracture as shown in FIG. 2C) inside the repositioned radius 100, and carries out work for placing the bone filling material C inside the space 108. In this work, a filling balloon 32 (refer to FIG. 1) arranged in the space 108 is filled with the paste-like bone filling material C. Then, the filling material C is left in a cured state after a predetermined amount of time elapses, and is exposed from the filling balloon 32. Then, if the filling balloon 32 is collected from the space 108, only the cured bone filling material C is placed inside the space 108.

After the placement of the bone filling material C, a wrist is fixed by a cast or the like, and a fixing state of the wrist is continued for a predetermined time period. During this time period, the bone filling material C is absorbed by easily and reliably being in contact with the bone near the placement site inside the radius 100. The absorbed bone filling material C is gradually substituted with the autologous bone, and augments the inside of the radius 100, thereby joining the body portion 100a and the distal end portion 100b to each other. In the treatment for placing this bone filling material C, it is possible to minimize the influence on surrounding tissues of the fracture site. Therefore, as compared to a treatment method in the related art which fixes the fracture site using a metal plate or a screw, the treatment can be safely carried out.

Referring back to FIG. 1, next, a configuration of the bone treatment system 10 will be described in detail. The bone treatment system 10 is a therapeutic kit for implementing the above-described placement measure, that is, bone filling material placement therapy for curing the uncured bone filling material C and placing the cured bone filling material C inside the bone. This bone filling system 10 includes a space forming device 12, a placement device 14, and a deployment operation device 16.

The bone treatment system 10 can employ several devices in addition to the above-described devices. For example, the bone treatment system 10 may include an opening/closing tool for incising or drilling into body tissues around a fracture site, a drill for drilling into the compact bone 104 of the radius 100, a cannula for building a guide path for the drill or the space forming device 12, and a fastener for maintaining a position of the repositioned bone. As these devices, known devices can be used, and thus, a detailed description of such devices will be omitted.

The space forming device 12 is a device for forming the space 108 (refer to FIG. 7A) in advance for placing the bone filling material C inside the repositioned radius 100. This space forming device 12 has a shaft 18, a space forming balloon 20 disposed on a distal side of the shaft 18, a hub 22 (grip portion) disposed on a proximal side of the shaft 18, and an inflating/deflating operation device 24 connected to the hub 22.

The shaft 18 is an elongated tubular member having a thickness by which the shaft 18 can reach the inside of the radius 100 from outside of the body. In order for the shaft 18 to relatively easily approach the inside of the radius 100 from outside of the body, it is preferable that the shaft 18 be configured to be made of a rigid material (for example, hard plastic or a metal material). A lumen 26, through which an inflating fluid is to flow is formed inside the shaft 18 such that the lumen penetrates the shaft 18 along an axial direction.

The space forming balloon 20 is a film member attached to a side surface of a distal end portion of the shaft 18. The lumen 26 communicates with an inner side portion (interior) of the space forming balloon 20, and the inflating fluid can be introduced into the balloon and discharged from the balloon via this lumen 26. In this manner, the space forming balloon 20 is inflated radially outward on the side surface of the distal end portion of the shaft 18, and exhibits a spherical shape in an inflated state. The shape of the inflated space forming balloon 20 is not limited to the spherical shape, and may be an elliptical shape in a side view, or may be a rounded shape as a whole. In addition, a horizontal cross-sectional shape of the inflated space forming balloon 20 is not limited to a circular shape (including a substantially circular shape), and may be the elliptical shape.

The space forming balloon 20 can be made of, for example, a non-elastic material. Examples of the non-elastic material include fibrous porous film such as textile, knitted fabric, non-woven fabric, and a paper material, and additionally dense film such as non-fibrous porous film and a polymer sheet. The space forming balloon 20 may be made of an elastic material. Examples of the elastic material include various rubber materials such as natural rubber, butyl rubber, isoprene rubber, butadiene rubber, styrene-butadiene rubber, silicone rubber, various thermoplastic elastomers such as a polyurethane system, a polyester system, a polyamide system, an olefin system, and a styrene system, or mixtures thereof.

In addition, the inflating fluid supplied to the space forming balloon 20 is also not particularly limited. For example, an X-ray contrast agent or physiological saline may be used. In particular, the X-ray contrast agent enables an operator to image an inflation degree of the space forming device 12 inside the radius 100 during X-ray photography, and thus, is advantageously used from a viewpoint of setting a post-filling amount for the bone filling material C.

The hub 22 disposed on the proximal side (end) of the shaft 18 possesses an outer diameter larger than that of the shaft 18 in order for a surgeon to easily operate the hub 22 when the surgeon manually operates the device. In addition, the hub 22 is formed as a Y-type connector so as to connect the inflating/deflating operation device 24 to the hub. An introduction space portion 22a which causes the inflating fluid supplied from the inflating/deflating operation device 24 to flow in the lumen 26 is disposed inside the hub 22.

The inflating/deflating operation device 24 is configured to, for example, have a syringe and is connected to an introduction port 28 of the hub 22 (Y-type connector). The inflating/deflating operation device 24 functions to supply the inflating fluid is supplied to the shaft 18 side and further to suction the supplied inflating fluid by an operation of the surgeon. For example, if the inflating/deflating operation device 24 is the syringe, the surgeon performs a pushing operation of a plunger so as to cause the inflating fluid to flow out from the syringe, and to supply the inflating fluid to the space forming balloon 20. In addition, after the inflating fluid is supplied, the surgeon takes off his or her hand from the plunger (or pulls out the plunger), thereby performing an operation for suctioning the inflating fluid.

The inflating/deflating operation device 24 may be configured so as to indicate a filling amount of the bone filling material C (alternatively, to indicate a supply amount itself of the inflating fluid), corresponding to an amount of the inflating fluid supplied to the space forming balloon 20. That is, a volume of the space 108 inside the radius 100 which is formed by the space forming device 12 is approximately equal to a volume of the supply amount of the inflating fluid. Therefore, the volume of the space 108 can be used as an index when filling the bone filling material C later. For example, the inflating/deflating operation device 24 may have a configuration in which the filling amount of the bone filling material C is jointly marked in a scale of the syringe and an advanced position of the plunger is automatically marked when the inflating fluid is supplied to the maximum amount. In this manner, based on the indicated filling amount of the bone filling material C, it is possible to accurately fill the bone filling material C later.

The space forming balloon 20 of the space forming device 12 is left in a deflated state until the space forming balloon is inserted into the radius 100, and then, is inflated in response to the supply of the inflating fluid inside the radius 100. The space forming balloon 20, while being inflated, crushes bone tissues inside the radius 100. The trabecular bone 106 inside the radius 100 suffering from the osteoporosis is brittle, and thus, is relatively easily crushed by the inflated space forming balloon 20. In contrast, the space forming balloon 20 has sufficient strength. Therefore, there is no damage such as a rupture or a hole forming. In this manner, the space 108 is formed inside the radius 100 in response to the inflated space forming balloon 20.

Figure 3:
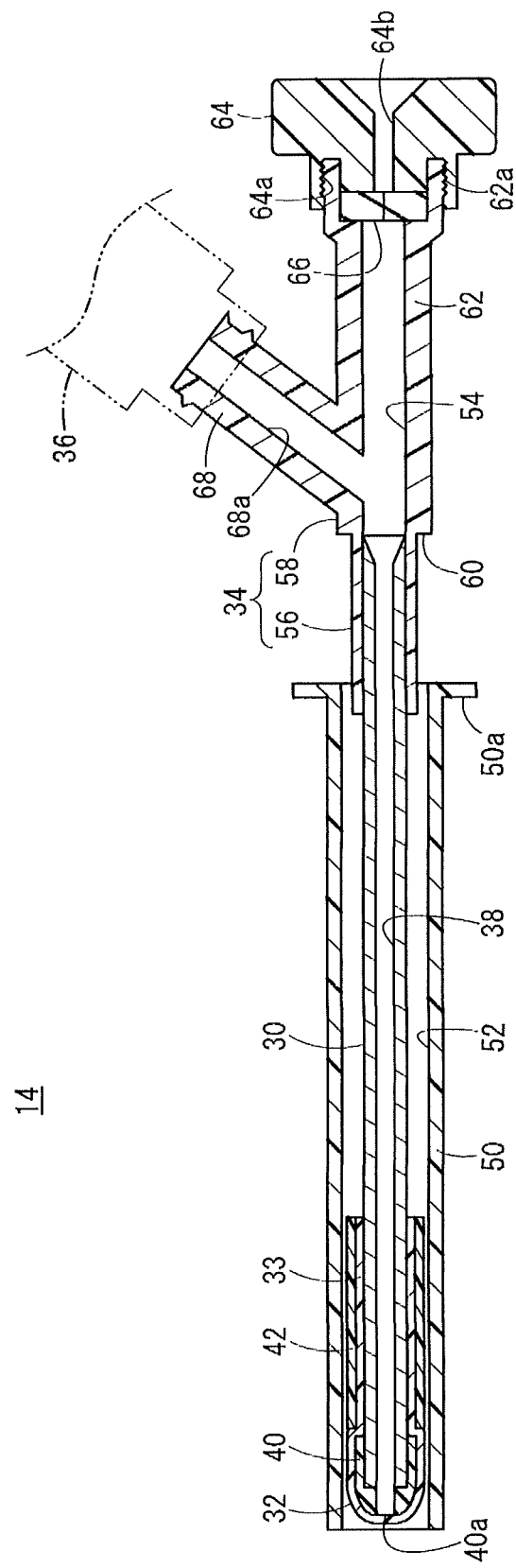
FIG. 3 is a side cross-sectional view of a placement device of the bone treatment system in FIG. 1.

After the space forming device 12 is used, the placement device 14 of the bone treatment system 10 illustrated in FIGS. 1 and 3 is used. The placement device 14 functions to place the bone filling material C in the space 108 formed inside the radius 100. The placement device 14 includes the shaft 30, the filling balloon 32 disposed on the distal side (distal end) of the shaft 30, a grip portion 34 disposed on the proximal side of the shaft 30, and a supply device 36 connected to the grip portion 34.

The shaft 30 possesses a length and a thickness which are substantially the same as those of the shaft 18 of the space forming device 12, and the rigidity of the shaft 30 is also approximately the same as the rigidity of the shaft 18. Examples of materials which can be used to fabricate the shafts 18 and 30 include metal materials such as stainless steel, aluminum alloys, and copper-based alloys, and resin materials such as polyolefin, polyvinyl chloride, polyamide, polyamide elastomer, polyester, polyester elastomer, polyurethane, polyurethane elastomer, polyimide, a fluorine resin, PEEK, polyethylene terephthalate, and the like.

A flow path 38 (lumen) through which flows the paste-like bone filling material C is formed inside the shaft 30 and extends along the shaft 30 in the axial direction. This flow path 38 possesses an inner diameter sufficiently larger than the outer diameter of the deployment operation device 16, and allows the deployment operation device 16 to pass through the flow path 38 even in a state where the deployment operation device 16 is fully filled with the bone filling material C. For example, the inner diameter of the flow path 38 is preferably set to 2 mm to 5 mm, and more preferably set to 2.5 mm to 4.5 mm.

In addition, as illustrated in FIGS. 3 and 4A, a tip 40 is attached to the distal end portion of the shaft 30. The tip 40 possesses a tapered shape in which a proximal portion side (proximal end) which is larger in outer diameter than the outer diameter of the shaft 30 is fixed to an outer peripheral surface of the shaft 30 and is tapered toward the distal end from the proximal portion. Also, the inner diameter of the proximal part of the tip 40 is greater than the outer diameter of the shaft 30.

This tip 40 is made of a material which is more flexible than that of the shaft 30. The material used to fabricate the tip 40 is not particularly limited. However, for example, it is preferable to form the tip 40 by using a material having a certain degree of flexibility. The tip 40 may be made of urethane resins or elastomeric materials such as polyurethane elastomer, polyester elastomer, and nylon elastomer. In addition, it is preferable that the tip 40 be configured to include a material to which an X-ray contrast-available imaging member can be attached, or an X-ray contrast-available material. This enables a surgeon to easily recognize a position of the distal end portion of the placement device 14 when inserting the placement device 14 or when filling the bone filling material C.

An outer surface of the tip 40 is covered with the filling balloon 32 in a deflated state. The flexible tip 40 supports the filling balloon 32 from inside so as not to be damaged. In addition, the tip 40 supports the filling balloon 32 from inside, in a state where the filling balloon 32 is inflated, without any wrinkles. Therefore, the tip 40 can smoothly inflate the filling balloon 32. The lumen of the tip 40 having an opening 40a communicates with the flow path 38 of the shaft 30. The opening 40a ejects the bone filling material C flowed in the flow path 38, in a distal end direction. In this manner, the opening 40a inflates the filling balloon 32 on the further distal side than the shaft 30. That is, the balloon 32 is inflated distally beyond the distal end of the shaft 30.

The filling balloon 32 has elasticity, and is configured so that a deflated state of coming into contact with the outer surface of the tip 40 can be transferred to an inflated state of being separated from the tip 40 in response to the supplied bone filling material C. The proximal end portion of the filling balloon 32 is fixed by a fixing tube 42. As illustrated in FIG. 4B, if the bone filling material C is supplied, the filling balloon 32 is inflated so that the balloon 32 exhibits a spherical shape. In this inflated state, the distal end of the shaft 30 and the tip 40 are located on the proximal side of the distal-most end of the inflated balloon 32 as seen in FIG. 4B. FIG. 4B shows that the distal-most end of the shaft 30 and the tip 40 are located between the center of the inflated balloon 32 and the proximal-most end of the inflated balloon 32.

The filling balloon 32 is configured to be more flexible than the space forming balloon 20, and becomes thinner by being greatly stretched (elastically deformed) when inflated. Therefore, when inflated inside the radius 100, the filling balloon 32 possesses a three-dimensional shape which is appropriately deformed in response to the shape of the space 108. The material forming the filling balloon 32 is not particularly limited. However, it is preferable to form the filling balloon 32 using a material having a certain degree of flexibility. For example, as this material, it is possible to use polyethylene, polypropylene, polybutene, ethylene-propylene copolymer, ethylene-vinyl acetate copolymer, ionomer, or mixtures of two or more type from among these such as polyolefin or soft polyvinyl chloride resins, thermoplastic resins such as polyamide, polyamide elastomer, polyester, polyester elastomer, polyurethane, polyurethane elastomers, nylon elastomer, and fluorocarbon resins, isoprene rubber, silicone rubber, latex rubber, or the like.

The inflated filling balloon 32 is configured to be broken (ruptured) rather easily by the deployment operation device 16. The cured bone filling material C after filling is exposed in the space 108 of the radius 100 by breaking this filling balloon 32. In the filling balloon 32, the proximal end portion is firmly fixed to the fixing tube 42. Accordingly, even after being broken, the balloon remains attached to the placement device 14 and so a state of being attached to the placement device 14 is maintained. As the placement device 14 is pulled out, the filling balloon 32 is also pulled out from the inside of the radius 100.

The fixing tube 42 is attached so as to surround the proximal end portion (fixing portion 33) of the filling balloon 32, and fixes the filling balloon 32 by interposing the filling balloon 32 between the shaft 30 and the fixing tube 42. This fixing tube 42 is of a predetermined length along the axial direction of the shaft 30 so as to firmly hold the proximal end portion of the filling balloon 32. As illustrated in FIG. 4A, a groove portion (groove) 44 extending in the axial direction is formed on an inner surface of the fixing tube 42 which comes into contact with the filling balloon 32.

Figure 5A:
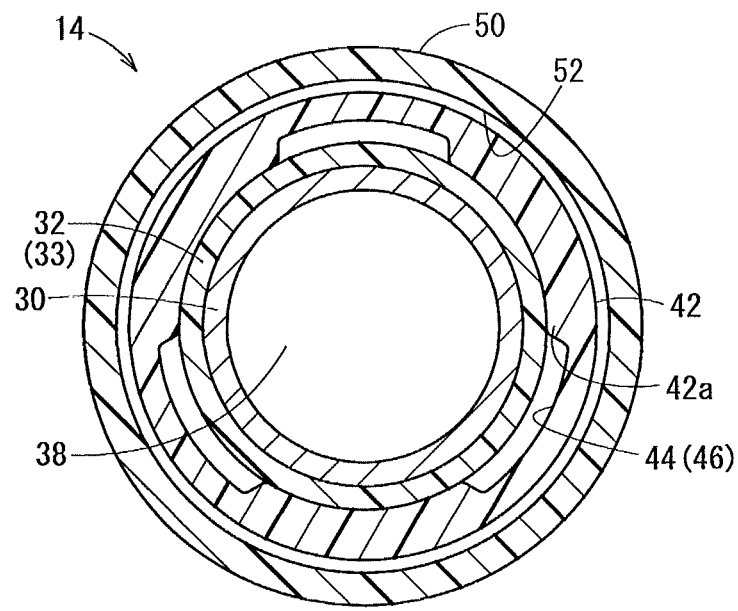
FIG. 5A is a cross-sectional view taken along the section line VA-VA in FIG. 4A.

This groove portion 44 functions as a gas discharge portion 46 which discharges air present in the shaft 30 or the filling balloon 32 when filling the bone filling material C. As illustrated in FIG. 5A, the groove portion 44 is disposed at multiple locations along a circumferential direction of an inner peripheral surface of the fixing tube 42. The filling balloon 32 is fixed by adjacent fixing walls 42a between the respective groove portions 44.

Figure 5B:
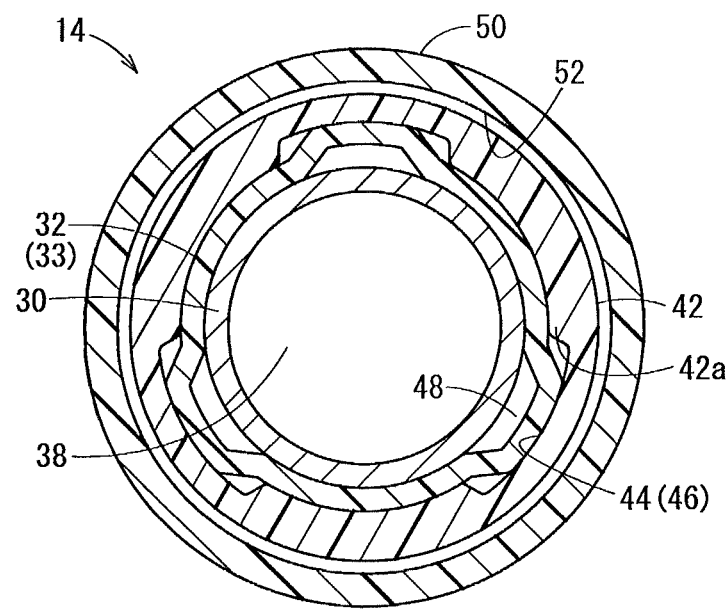
FIG. 5B is a cross-sectional view illustrating deformation of the filling balloon when filling a bone filling material, subsequent to FIG. 5A.

The fixing portion 33 of the filling balloon 32 closely adheres to the outer peripheral surface of the shaft 30 over the entire periphery, before the bone filling material C is supplied. Then, when the bone filling material C is supplied, the air internally present in the flow path 38 is pushed out to the filling balloon 32 side. As illustrated in FIG. 5B, the fixing portion 33 is elastically deformed toward the groove portion 44, thereby forming an air discharge path 48. In this manner, the air is discharged from the proximal side of the fixing tube 42 via the air discharge path 48, thereby minimizing air mixture in the bone filling material C. By setting this groove portion 44 to have a reasonably small depth or width, it is possible to prevent the bone filling material C from leaking out from the air discharge path 48.

Referring back to FIG. 3, when inserted into the radius 100, the placement device 14 includes the shaft 30, the filling balloon 32, and a tubular sheath 50 which protects the tip 40. The sheath 50 has an accommodation lumen 52 (accommodation portion) whose inner diameter is larger than the outer diameter of the fixing tube 42, and accommodates the shaft 30 or the filling balloon 32 so as to be slidable.

The sheath 50 is formed to have a length which is slightly longer than that of the shaft 30 (length from the tip 40 through the vicinity of the distal end of the grip portion 34). An operation plate 50a (sheath operation portion) protruding radially outward is disposed in the proximal end portion of the sheath 50. The sheath 50 is moved forward and rearward relative to the shaft 30 by a surgeon operating the operation plate 50a in the proximal end direction or in the distal end direction. The filling balloon 32 is exposed from the distal end of the sheath 50 by the rearward movement of the sheath 50.

The grip portion 34 of the placement device 14 is configured to have a Y-type connector, similar to the space forming device 12. An introduction space portion 54 communicating with the flow path 38 of the shaft 30 is formed inside the grip portion 34 by penetrating the grip portion 34. The grip portion 34 has a tubular distal end portion 56 formed to have the outer diameter which is smaller than the inner diameter of the accommodation lumen 52, and a tubular body portion 58 which is connected to the proximal end of the tubular distal end portion 56 and has a diameter larger than that of the tubular distal end portion 56. Therefore, a step 60 which opposes the proximal end portion of the sheath 50 and regulates a rearward movement limit of the sheath 50 is formed between the tubular distal end portion 56 and the tubular body portion 58.

The tubular body portion 58 is a portion gripped by a surgeon when the placement device 14 is used, and is formed so as to coincide with an axial center of the shaft 30. That is, the tubular body portion 58 and the shaft 30 are coaxial. The proximal side of this tubular body portion 58 is configured to serve as an insertion port 62 which enables the deployment operation device 16 to be inserted into the flow path 38.

A male screw portion 62a is formed on the outer peripheral surface of the proximal end of the insertion port 62, and a guide member 64 having a female screw portion 64a is attached to this male screw portion 62a. The guide member 64 includes an insertion hole 64b which coincides with the axial center of the introduction space portion 54 in an attachment state of the guide member 64. That is, the insertion hole 64b and the introduction space portion 54 are coaxial. This insertion hole 64b possesses an inner diameter which is slightly larger than the outer diameter of the deployment operation device 16 (mandrel 70). A valve body 66 is disposed between the guide member 64 and the grip portion 34. Whereas the valve body 66 allows and guides the deployment operation device 16 to be inserted, the valve body 66 functions to prevent leakage of the bone filling material C.

In addition, an injection port 68 obliquely protruding in the proximal end direction is disposed on a side portion of the tubular body portion 58. The injection port 68 internally has an introduction path 68a for introducing the bone filling material C to the introduction space portion 54. An attachment portion (Luer-lock mechanism) to which the supply device 36 is detachably attached is disposed in the proximal end portion thereof.

The supply device 36 is a device for filling of the bone filling material C, and for example, is configured to have a syringe, similar to the inflating/deflating operation device 24. A surgeon performs a pushing operation of a plunger, and accordingly the supply device 36 discharges the bone filling material C from the distal end portion attached to the attachment portion of the injection port 68. In this manner, the bone filling material C is supplied to the flow path 38 of the shaft 30 via the introduction path 68a and the introduction space portion 54.

The bone filling material C supplied to the flow path 38 flows in the distal end direction of the shaft 30. At this time, the air inside the shaft 30 is discharged outward (to the accommodation lumen 52 of the sheath 50) from the shaft 30 and the filling balloon 32 by the gas discharge portion 46 as described above. Accordingly, the bone filling material C is smoothly guided in the distal end direction, and fills the inside of the filling balloon 32. The filling balloon 32 is left in an inflated state as illustrated in FIG. 4B, in the distal end portion of the shaft 30, in response to the filling of the bone filling material C. After filling the bone filling material C, the bone filling material C is allowed to cure for a predetermined amount of time (for example, approximately 5 minutes to 15 minutes) to a placement-available degree inside the radius 100.

Referring back to FIG. 1, the deployment operation device 16 is a device for exposing the above-described cured bone filling material C in the space 108 of the radius 100. This deployment operation device 16 is configured to include a mandrel 70 (insertion member) to be inserted before the bone filling material C is cured, and a needle member 80 to be inserted after the bone filling material C is cured and the mandrel 70 is pulled out.

The mandrel 70 is a rod member formed in an elongated linear shape, and has an elongated portion 71 whose length in the longitudinal direction is longer than that of the placement device 14, and whose outer diameter is smaller than the inner diameter of the flow path 38 of the placement device 14. The mandrel 70 is inserted into the inner surface on the distal side of the inflated filling balloon 32 through the flow path 38 of the placement device 14. This mandrel 70 is inserted into the paste-like bone filling material C, thereby forming a passage 72 (refer to FIG. 8B) inside the bone filling material C, when the bone filling material C is cured. The passage 72 is a hollow portion having a linear shape from the proximal end portion of the grip portion 34 (insertion port 62) to the inflated filling balloon 32.

It is preferable that the elongated portion 71 of the mandrel 70 be configured to have an X-ray contrast-available material so as to easily recognize a relative position of the mandrel 70 with respect to the filling balloon 32. In addition, it is preferable that a distal end portion 70a of the mandrel 70 be formed as a rounded tip so as not to be broken even when coming into contact with the inflated filling balloon 32.

When inserted, an orientation of the mandrel 70 is guided by the guide member 64 attached to the grip portion 34, and the valve body 66. In addition, in a state where the distal end portion 70a reaches the filling balloon 32, the proximal end portion is held by the valve body 66. In this manner, the orientation is excellently maintained until the bone filling material C is cured. In order for the mandrel 70 to facilitate a forward movement operation, it is preferable that an operation portion 74 whose diameter is larger than that of the mandrel 70 be attached to the proximal end portion of the elongated portion 71. The operation portion 74 may be formed so as to be held by the insertion hole 64b in an insertion state of the mandrel 70 by forming the operation portion 74 to have the outer diameter which coincides with the inner diameter of the insertion hole 64b of the guide member 64.

When the predetermined amount of time elapses after the mandrel 70 is inserted into the placement device 14 and the passage 72 is formed in the cured bone filling material C, the mandrel 70 is pulled out from the placement device 14 by a surgeon. The outer peripheral surface of the elongated portion 71 is relatively smoothly formed. The mandrel 70 can be relatively easily pulled out by being slightly vibrated or rotated. The elongated portion 71 may be coated with a lubricant 71a (lubricant for the insertion member) which facilitates a relative movement for the cured bone filling material C. For example, the lubricant 71a includes silicone oil or the like. After the mandrel 70 is pulled out, the needle member 80 is inserted into the passage 72.

Similar to the mandrel 70, the needle member 80 possesses an elongated linear shape, and has a sharp needle tip 82 in the distal end portion. The needle member 80 possesses an outer diameter which is slightly smaller than the outer diameter of the mandrel 70, and can smoothly pass through the passage 72 of the bone filling material C which is previously formed by the mandrel 70. The needle tip 82 of the needle member 80 moves together with the placement device 14 in the distal end direction and comes into contact with the inflated filling balloon 32. In this manner, the needle tip 82 can rather easily break the filling balloon 32. To increase sliding performance of the needle member 80, similar to the mandrel 70, the outer peripheral surface of the needle member 80 may be coated with the lubricant 71a.

The material forming the mandrel 70 or the needle member 80 is not particularly limited. For example, the mandrel 70 or the needle member 80 may be made of a metal material such as stainless steel. In addition, it is preferable that the needle member 80 also be X-ray contrast-available. In this manner, when the forward movement operation of the needle member 80 is performed, it is possible to recognize that the needle tip 82 reaches the filling balloon 32 and breaks the filling balloon 32.

The bone treatment system 10 according to the present embodiment is basically configured as described above. Next, an operation effect of the bone treatment system 10 will be described.

Hereinafter, as an example of bone treatment using the bone treatment system 10, treatment for a distal radius fracture which is performed by placing the bone filling material C will be described. As illustrated in FIG. 2B, a surgeon repositions a fracture site of the radius 100 before implementing a placement measure, and arranges a normal positional relationship between the tubular body portion 100a and the distal end portion 100b. Then, the placement measure is implemented for the repositioned radius 100. In the subsequent placement measure, X-ray photography is carried out, and a state of the fracture site of the radius 100 is confirmed on a real-time basis by using an X-ray photographed image.

Figure 6A:
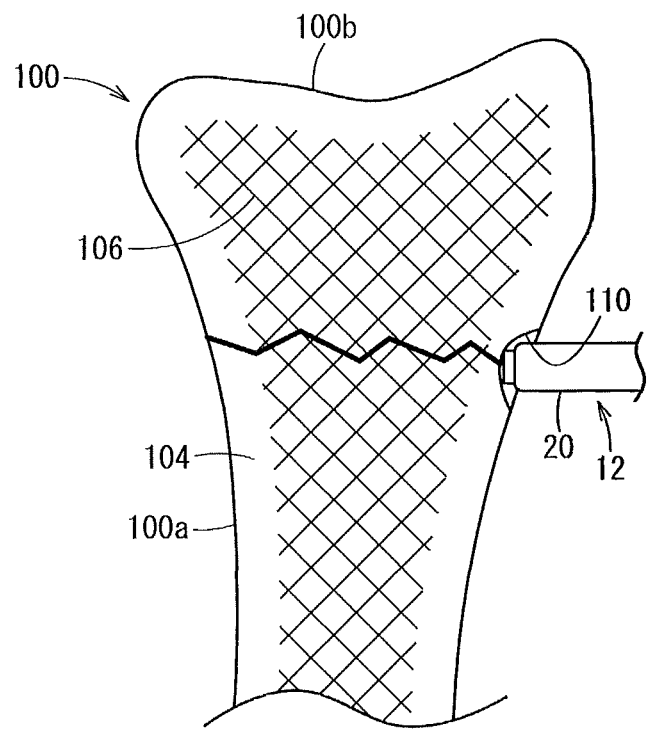
FIG. 6A is a first illustrating view for illustrating a placement measure of the bone filling material using the bone treatment system in FIG. 1.

As illustrated in FIG. 6A, in the placement measure, the space forming device 12 is first used. The surgeon holds a repositioned state and incises the skin. Then, the surgeon forms a hole 110 for inserting the space forming device 12 and the placement device 14 with respect to the compact bone 104 of the radius 100 by using a drill or the like. It is preferable that the hole 110 be drilled along a site cracked due to the fracture. In this manner, it is possible to rather easily insert the space forming device 12 or the placement device 14 into the hole 110 later. A drilling direction of the hole 110 with respect to the radius 100, in other words, an inserting direction of the space forming device 12 or the placement device 14 is not particularly limited. The direction may be appropriately set depending on fracture conditions.

After the hole 110 is formed, the space forming device 12 is inserted into the hole 110. At this time, the space forming balloon 20 is in a deflated state, and thus, the distal end portion of the space forming device 12 is rather easily inserted into the radius 100. In addition, the trabecular bone 106 inside the radius 100 is brittle due to the osteoporosis. Accordingly, the space forming device 12 is allowed to enter the inside of the radius 100.

Figure 6B:
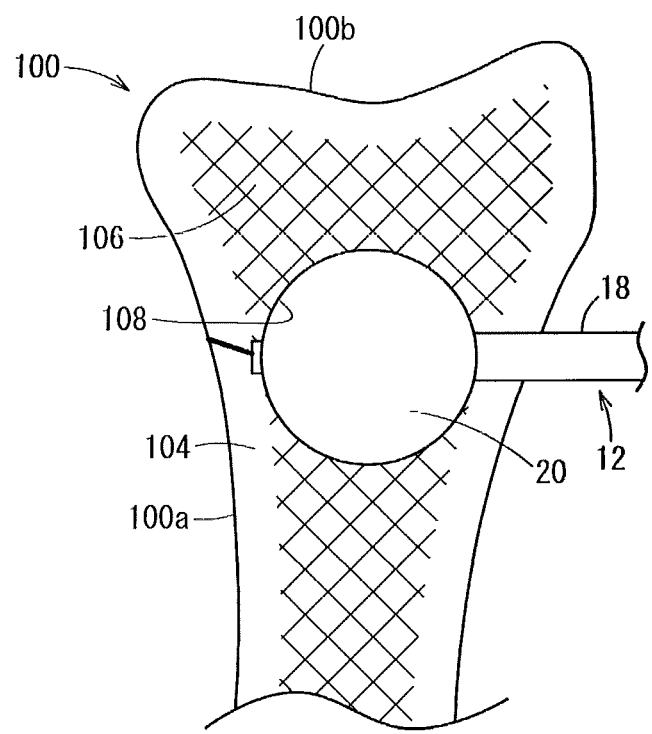
FIG. 6B is a second illustrating view for illustrating the placement measure of the bone filling material, subsequent to FIG. 6A.

As illustrated in FIG. 6B, after the surgeon inserts the distal end portion of the space forming device 12 into a rear portion (compact bone 104 on a side opposite to the hole 110) of the radius 100, the surgeon inflates the space forming balloon 20 by supplying the inflating fluid. The space forming balloon 20 has sufficient strength, and thus, crushes the trabecular bone 106, which is brittle, due to supplied pressure of the inflating fluid when the space forming balloon 20 is inflated and contacts the bone. In this manner, the space 108 is formed inside the radius 100 in response to an inflated amount (volume) of the space forming balloon 20. After the space 108 is formed, the space forming balloon 20 is deflated and the space forming device 12 is pulled out from the inside of the radius 100.

Figure 7A:
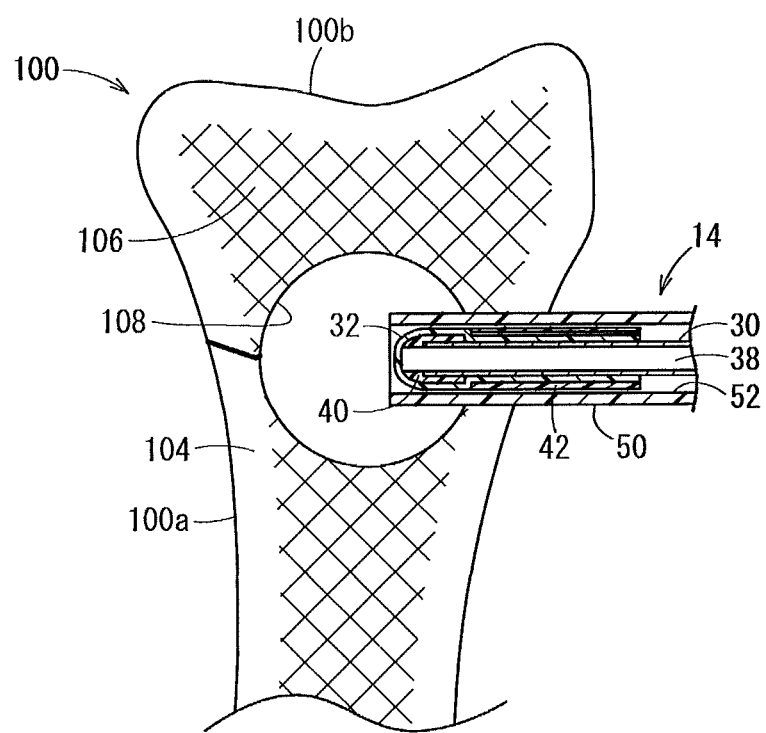
FIG. 7A is a third illustrating view for illustrating the placement measure of the bone filling material, subsequent to FIG. 6B.

Next, as illustrated in FIG. 7A, the placement device 14 is used instead of the space forming device 12. In a state where the shaft 30 and the filling balloon 32 are accommodated in the accommodation lumen 52 of the sheath 50, the surgeon causes the placement device 14 to move forward to the radius 100 and inserts the placement device 14 into the hole 110 (refer to FIG. 6A). At this time, the sheath 50 is also inserted into the radius 100. In this manner, it is possible to avoid damage to the filling balloon 32. In addition, it is possible to recognize an insertion amount of the device with respect to the radius 100 from outside of the body. When the placement device 14 is inserted, the sheath 50 may be used for alignment of the hole 110, outside the radius 100. The shaft 30 or the filling balloon 32 may be inserted into the radius 100 by being caused to move forward with respect to the sheath 50.

When the distal end portion of the placement device 14 is inserted into the space 108, the operation plate 50a of the sheath 50 is caused to move rearward in the proximal end direction. Then, the distal end portion of the shaft 30 (deflated filling balloon 32) is exposed inside the space 108. The sheath 50 is caused to perform a rearward movement operation until the proximal end portion comes into contact with the step 60 of the grip portion 34. In this manner, the filling balloon 32 can be reliably inflated.

Figure 7B:
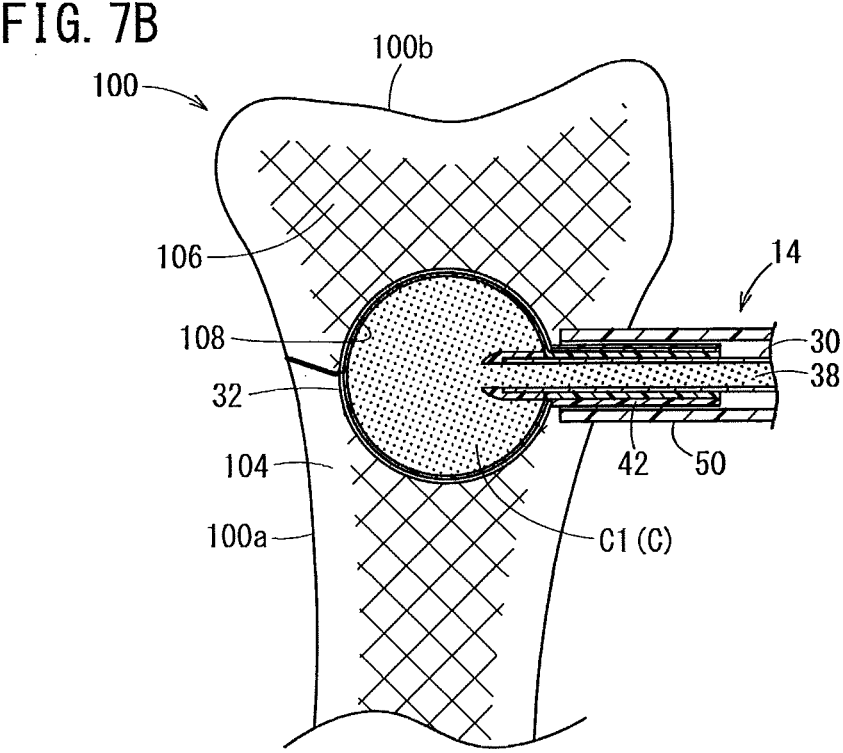
FIG. 7B is a fourth illustrating view for illustrating the placement measure of the bone filling material, subsequent to FIG. 7A.

After the sheath 50 is caused to move rearward, the surgeon operates the supply device 36. As illustrated in FIG. 7B, the paste-like bone filling material C is supplied to the filling balloon 32 through the flow path 38 of the shaft 30. In the following description, the reference number C1 will be given to a paste-like bone filling material, and the reference number C2 will be given to a bone filling material left in a cured state (state of being cured to such an extent so as not to be disintegrated by at least body fluid, or a more cured state). When the bone filling material C1 is supplied, the air inside the flow path 38 is pulled out (discharged) to the accommodation lumen 52 of the sheath 50 by the gas discharge portion 46 (refer to FIG. 5B), and is discharged to the outside of the body from the proximal end portion of the sheath 50.

The filling balloon 32 is inflated at the distal end of the shaft 30 by virtue of the bone filling material C1 filling the inside of the filling balloon 32 so that the inflated balloon corresponds in shape to a shape of the space 108. It is preferable to set an inflated amount of the filling balloon 32 to such an extent so as to substantially coincide with or be slightly smaller than the volume of the space 108. This prevents the filling balloon 32 from being strongly pressed between the bone filling material C2 and the inner surface of the radius 100 due to the excessive filling of the bone filling material C1. Therefore, it is possible to smoothly collect (remove) the filling balloon 32 later.

Figure 8A:
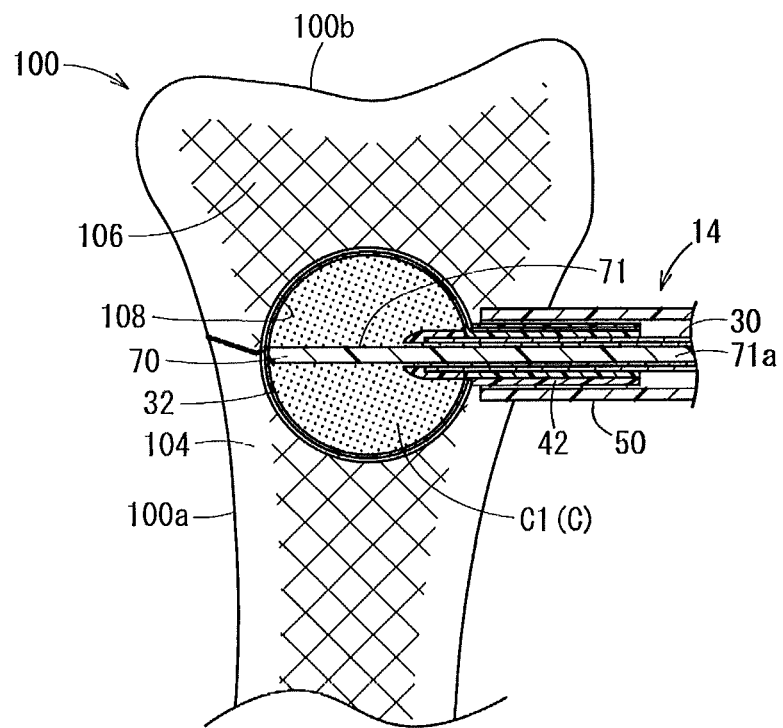
FIG. 8A is a fifth illustrating view for illustrating the placement measure of the bone filling material, subsequent to FIG. 7B.

After the filling balloon 32 is inflated, the mandrel 70 (deployment operation device 16) is inserted through the insertion port 62 of the placement device 14. The surgeon causes the mandrel 70 to perform the forward movement operation in the distal end direction via the flow path 38 of the placement device 14. As illustrated in FIG. 8A, the distal end portion 70a comes into contact with the inner surface of the filling balloon 32, thereby stopping the forward movement of the mandrel 70. In the mandrel 70, a position of the distal end portion 70a is confirmed during the X-ray photography. Accordingly, it is possible to prevent the mandrel 70 from being unnecessarily pushed out to the filling balloon 32 and breaking the filling balloon 32 before the bone filling material C1 is cured.

The timing for inserting the mandrel 70 into the placement device 14 is not particularly limited. In this manner, when the mandrel 70 is inserted after the filling of the bone filling material C1, it is possible to suppress an increase in liquid pressure of the bone filling material C1.

After the mandrel 70 is inserted, the surgeon causes the bone filling material C1 to be cured for a predetermined waiting time. For example, if the bone filling material C is a curable CPC, the bone filling material C is cured within approximately 10 minutes to such an extent so as not to be easily disintegrated due to the body fluid. Thus, in this example, the bone filling material is allowed to cure for 10 approximately minutes. Therefore, a patient does not feel a heavy burden.

After the predetermined amount of time elapses, the surgeon performs an operation for pulling out the mandrel 70 from the cured bone filling material C2. The linearly formed mandrel 70 can be smoothly pulled out along the axial direction of the placement device 14 without being disadvantageously caught on the bone filling material C2.

Figure 8B:
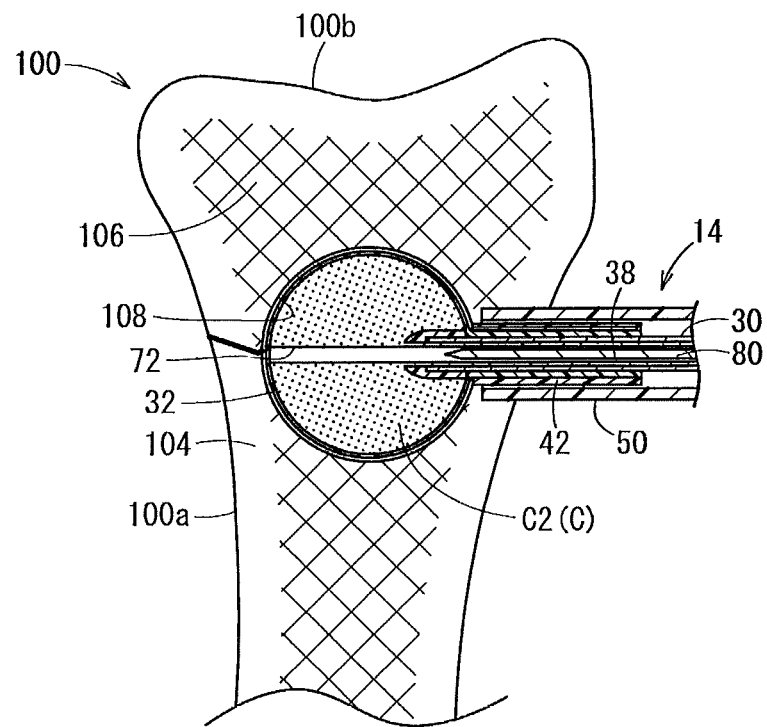
FIG. 8B is a sixth illustrating view for illustrating the placement measure of the bone filling material, subsequent to FIG. 8A.

When the mandrel 70 is pulled out, as illustrated in FIG. 8B, the passage 72 is formed inside the cured bone filling material C2. The passage 72 leads to the insertion port 62 of the placement device 14 into which the mandrel 70 is inserted. The surgeon inserts the needle member 80 through the insertion port 62, thereby enabling the needle member 80 to move forward along the passage 72.

Figure 9A:
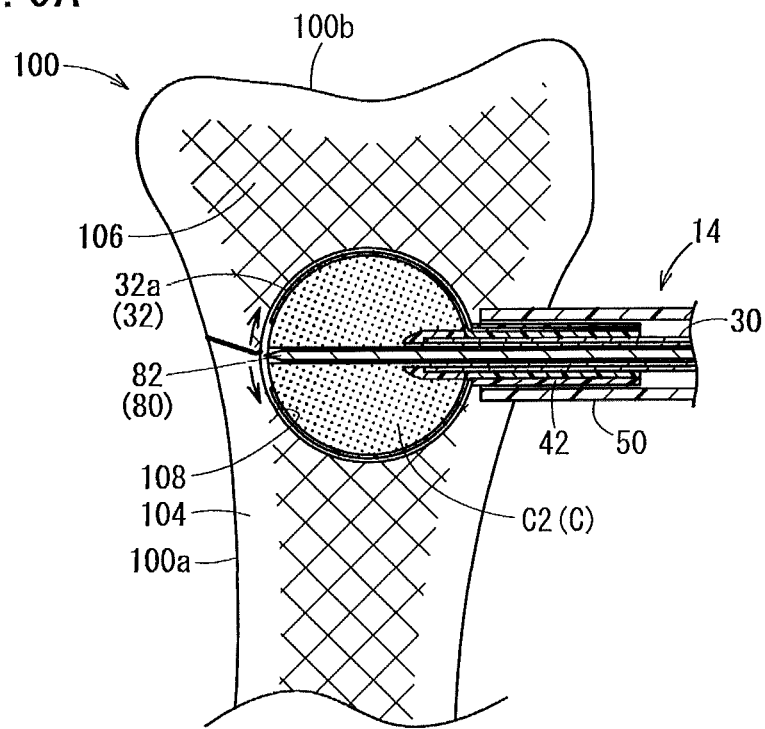
FIG. 9A is a seventh illustrating view for illustrating the placement measure of the bone filling material, subsequent to FIG. 8B.

The passage 72 possesses a linear shape extending to the inner surface of the filling balloon 32. Accordingly, the surgeon can smoothly perform the forward movement operation of the needle member 80 along the passage 72, and can easily cause the needle tip 82 to come into contact with a substantially center position of the filling balloon 32 opposing the passage 72. This contact of the needle tip 82 causes the filling balloon 32 to be broken from the rear side of the space 108 as illustrated in FIG. 9A. FIG. 9A illustrates a state immediately after the filling balloon 32 is ruptured. The needle tip 82 pierces the most stretched portion within the inflated filling balloon 32. Accordingly, this prompts the filling balloon 32 to be actively ruptured. In this manner, the cured bone filling material C2 is exposed inside the space 108.

The flexible filling balloon 32 is broken from the distal side (distal portion side) of the placement device 14. Accordingly, the filling balloon 32 is actuated so that a broken film portion (ruptured piece 32a) is moved to the proximal end portion side which is fixed to the shaft 30. That is, the ruptured piece 32a is moved inside the space 108 and comes close to the shaft 30 side, thereby actively exposing the bone filling material C2. In addition, the placement device 14 can rather easily collect the filling balloon 32 (ruptured piece 32a) which is moved to the proximal end portion side.

Figure 9B:
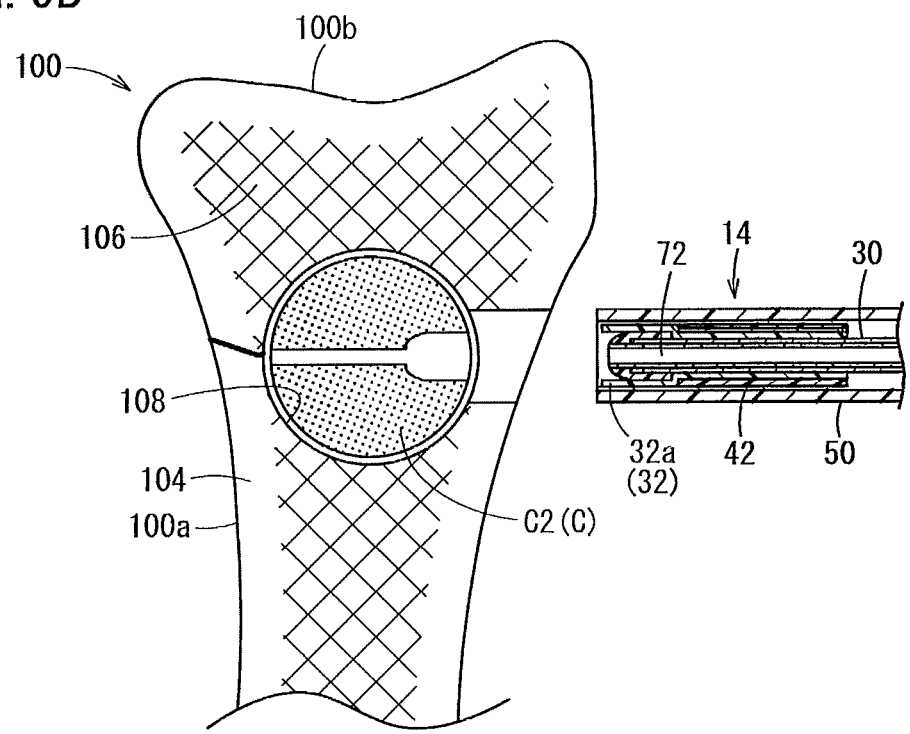
FIG. 9B is an eighth illustrating view for illustrating the placement measure of the bone filling material, subsequent to FIG. 9A.

After the bone filling material C2 is exposed, as illustrated in FIG. 9B, the needle member 80 is pulled out from the passage 72, and the placement device 14 is further pulled out from the inside of the radius 100. In this manner, the cured bone filling material C2 is placed in the space 108 of the radius 100.

The cured bone filling material C2 is absorbed in the bone near the inner periphery of the radius 100, and then is gradually substituted with the autologous bone. As a result, in the radius 100, the tubular body portion 100a and the distal end portion 100b are joined to each other.

As described above, according to the bone treatment system 10 of the present embodiment, it is possible to relatively easily place the cured bone filling material C2 with respect to the radius 100 by providing the placement device 14 and the deployment operation device 16. That is, during the fracture treatment, the mandrel 70 is inserted into the flow path 38 of the shaft 30 before the bone filling material C fills the inside of the filling balloon 32 and the bone filling material C is cured. Therefore, when the bone filling material C is cured, the passage 72 is formed inside the bone filling material C. In this manner, it is possible to rupture the filling balloon 32 by inserting the needle member 80 into the passage 72. Accordingly, the bone filling material C is rather easily exposed. In this manner, it is possible to favorably treat the bone by accurately placing the cured bone filling material C in the space 108. In particular, the bone filling material C which is likely to be disintegrated or poorly cured upon coming into contact with the body fluid when injected can be placed inside the radius 100 by minimizing the influence of the body fluid and in a state where the bone filling material C is more reliably cured. Accordingly, it is possible to improve the strength of the fracture site and to increase the therapeutic effect.

The placement device 14 can firmly fix the filling balloon 32 between the shaft 30 and the fixing tube 42. Accordingly, it is possible to reliably fill the inside of the filling balloon 32 with the bone filling material C, and it is possible to easily collect the filling balloon 32 after the bone filling material C is exposed from the filling balloon 32. Also, the filling balloon 32 expands or inflates in a forward or distal direction so that the expanded or inflated balloon is positioned distally beyond the distal-most end of the shaft 30 and the placement device 14.

In addition, in the placement device 14, the flexible tip 40 is attached to the distal end of the shaft 30. Accordingly, it is possible to support the filling balloon 32 without damaging the inner side of the balloon. Furthermore, since the placement device 14 includes the sheath 50, it is possible to protect the filling balloon 32 by using the sheath 50 when the placement device 14 is inserted. Then, after the placement device 14 is inserted, it is possible to rather easily inflate the filling balloon 32 by causing the sheath 50 to move rearward.

The inventive bone treatment system 10 disclosed here is not limited to the above-described configurations, and can adopt various modification examples and application examples. Hereinafter, some specific examples of modified examples of the bone treatment system 10 will be described. In the following description, the same reference numerals are given to features and aspects of the bone treatment system that are the same as those of the bone treatment system 10 described above, and a detailed description of such features and aspects will not be repeated.

A placement device 14A according to a first modification example illustrated in FIG. 10A does not include the tip 40 of a shaft 120. Instead, the filling balloon 32 is attached to an outer peripheral surface of a distal end portion of the shaft 120. A corner portion 120a on the outer peripheral surface side of the distal end portion of this shaft 120 is rounded, supports the deflated filling balloon 32 in an inflated state, and allows rather inflation of the filling balloon 32. As described above, the placement device 14A has a configuration from which the tip 40 is omitted. Accordingly, it is possible to reduce the manufacturing costs by decreasing the number of components. In addition, the distal end positions of the fixing tube 42 and the filling balloon 32 substantially coincide with each other. Accordingly, only an empty hole corresponding to the outer diameter of the deployment operation device 16 is formed inside the placed bone filling material C2. As illustrated in FIG. 9B, a large empty hole corresponding to the tip 40 is not left. Therefore, it is possible to increase the strength of the bone filling material C2.

Furthermore, the fixing tube 122 can protect the filling balloon 32 when the placement device 14A is inserted. Accordingly, the placement device 14A can adopt a configuration in which the sheath 50 is omitted.

A placement device 14B according to a second modification example illustrated in FIG. 10B has the shaft 120 of the first modification example shown in FIG. 10A, and also includes a filling balloon 130 is configured to have a non-elastic material. Therefore, it is preferable that the filling balloon 130 be accommodated in the shaft 120 when the placement device 14B is delivered into the radius 100. In this manner, the non-elastic filling balloon 130 is also inserted into the radius 100 without being caught on the radius 100 or the like. In addition, the bone filling material C flowed in the flow path 38 of the shaft 120 can inflate the filling balloon 130 in the distal end direction of the shaft 120 while pushing out the filling balloon 130. The filling balloon 130 is actuated so that the needle member 80 pierces the filling balloon 130 to be broken. If the placement device 14B is caused to move rearward, it is possible to expose the bone filling material from the broken portion.

Figure 11A:
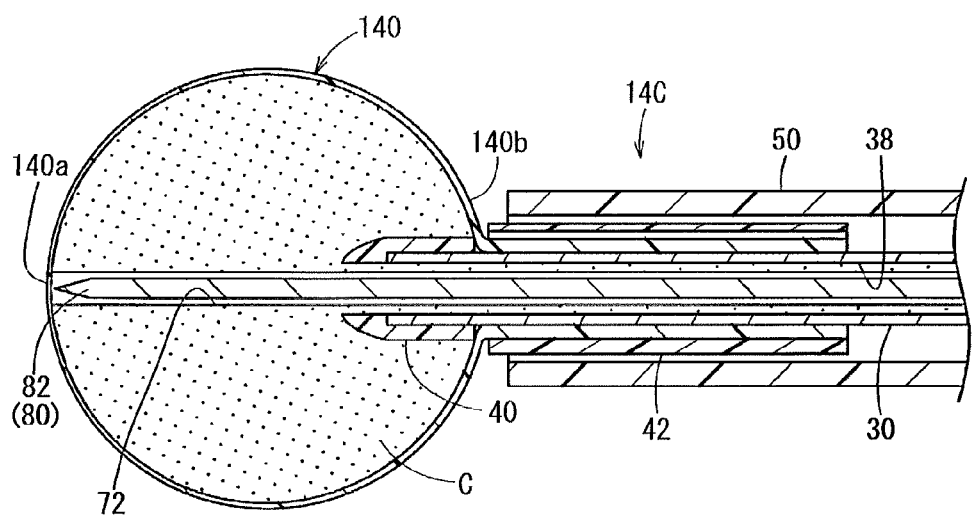
FIG. 11A is a side cross-sectional view illustrating a placement device according to a third modification example.

A placement device 14C according to a third embodiment illustrated in FIG. 11A has a configuration in which the thickness of the inflated filling balloon 140 varies depending on a location. Specifically, a location 140a which is the farthest away from the shaft 30 (around the distal end portion of the passage 72 in FIG. 11A) is relatively thin. A location 140b which comes close to the shaft 30 (around the proximal end portion fixed by the fixing tube 42) is relatively thick. By changing the thickness of the inflated filling balloon 140 in this way, it is possible to more easily rupture the filling balloon 140 or to more easily collect the filling balloon 140.

That is, the needle member 80 pierces the relatively thin location 140a of the filling balloon 140. Therefore, the filling balloon 140 is more easily broken and the rupture is prompted. In addition, in the broken filling balloon 140, the thick location 140b (proximal end portion) is drawn by a strong elastic force, and accordingly, the ruptured piece when broken can be more easily moved to the proximal side.

Figure 11B:
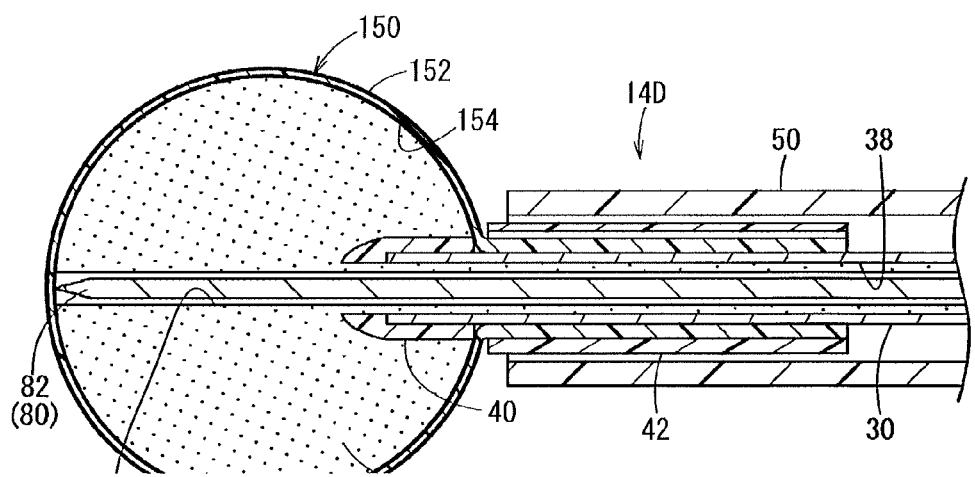
FIG. 11B is a side cross-sectional view illustrating a placement device according to a fourth modification example.

A placement device 14D according to a fourth modification example illustrated in FIG. 11B has a configuration in which lubricant coating layers 152 and 154 are disposed on the outer peripheral surface and the inner peripheral surface of a filling balloon 150. The lubricant coating layer 152 on the outer peripheral surface side is configured to cause the filling balloon 150 to slide with respect to the radius 100, and the lubricant coating layer 154 on the inner peripheral surface side is configured to cause the filling balloon 150 to slide with respect to the cured bone filling material C. When the filling balloon 150 is broken, the lubricant coating layers 152 and 154 prompt the filling balloon 150 to move to the proximal side. In this manner, it is possible to more reliably collect or remove the filling balloon 150. The lubricant may coat any one of the outer peripheral surface and the inner peripheral surface of the filling balloon 150, of course.

Figure 12A:
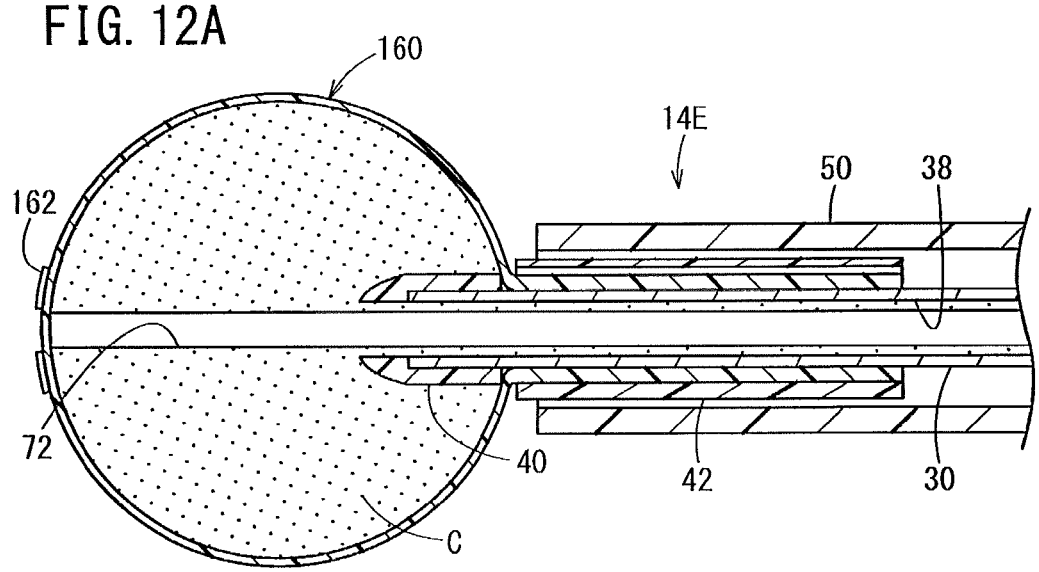
FIG. 12A is a first illustrating view for illustrating a placement device according to a fifth modification example.
Figure 12B:
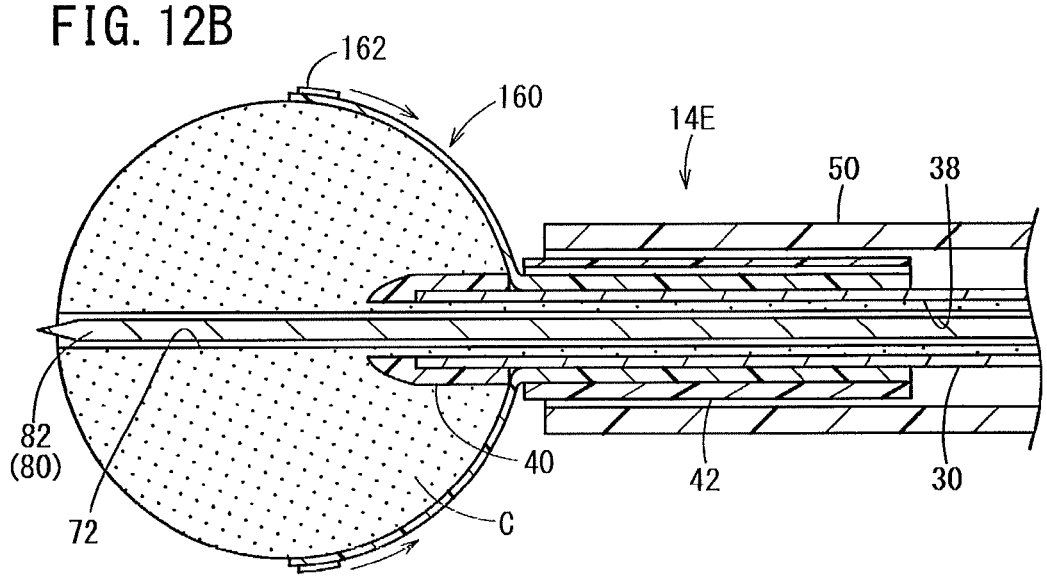
FIG. 12B is a second illustrating view for illustrating the placement device according to the fifth modification example.

A placement device 14E according to a fifth modification example illustrated in FIGS. 12A and 12B has a configuration in which an X-ray contrast-available imaging marker 162 (imaging portion) is disposed around the distal end portion of an inflated filling balloon 160. For example, the imaging marker 162 can be configured by forming a thin film using a metal material such as Cu, Au, Pt, and the like. The imaging marker 162 is disposed in this manner, thereby confirming separation of the imaging marker 162 from the shaft 30 when the filling balloon 160 is filled with the bone filling material C. Therefore, it is possible to confirm an inflated state of the filling balloon 160.

Then, when the filling balloon 160 is broken, the imaging marker 162 is also moved in response to a size decrease in the filling balloon 160 (movement to the proximal side). Therefore, it is possible to confirm that the filling balloon 160 is broken. In addition, by confirming the imaging marker 162, it is also possible to recognize that the ruptured piece of the filling balloon 160 is left inside the bone. A position or a range of the imaging portion disposed in the filling balloon 160 is not particularly limited. For example, the imaging portion may be disposed in the entire body of the filling balloon 160.

Figure 13A:
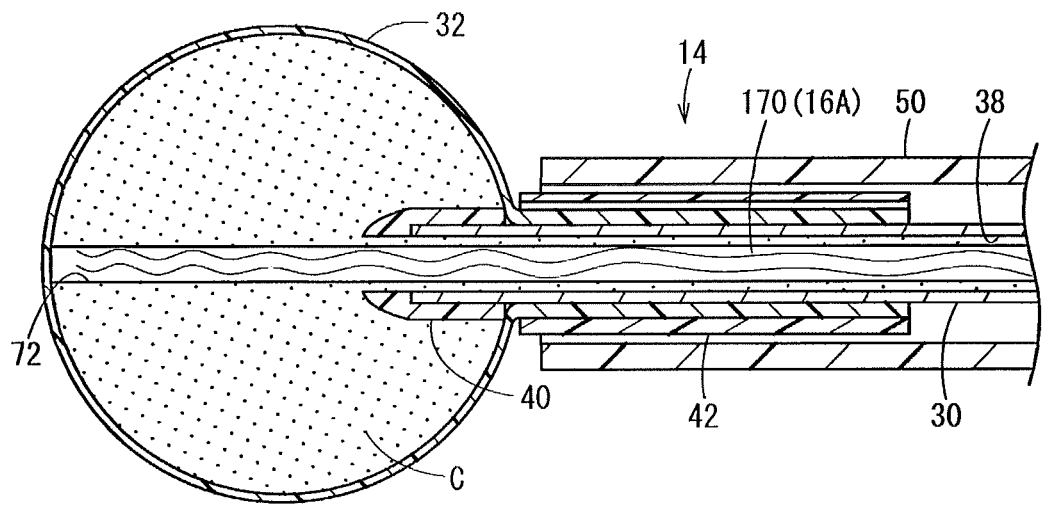
FIG. 13A is a side cross-sectional view illustrating a placement device according to a sixth modification example.

A deployment operation device 16A according to a sixth modification example illustrated in FIG. 13A has a configuration of supplying a solution 170 for rupturing (dissolving) the filling balloon 32 via the passage 72 after the passage 72 of the bone filling material C is formed by the mandrel 70. The solution 170 depends on the configuring materials of the filling balloon 32. However, for example, if the filling balloon 32 is styrene-based elastomer, the solution 170 includes soybean oil, Lipiodol (registered trademark), and the like. As described above, the deployment operation device 16A may expose the bone filling material C by supplying the solution 170 on behalf of the needle member 80. In short, the configuration or manner of breaking the filling balloon 32 is not particularly limited, and various configurations can be adopted. For example, as an actuating member instead of the above-described needle member 80, a device including a heating portion in the distal end portion may be inserted into the passage 72. The heating portion may cut off a portion of the filling balloon 32, thereby rupturing the filling balloon 32. Alternatively, as other actuating members, a device including a scissoring mechanism in the distal end portion may be inserted into the passage 72. The scissoring mechanism may cut off a portion of the filling balloon 32, thereby rupturing the filling balloon 32.

Figure 13B:
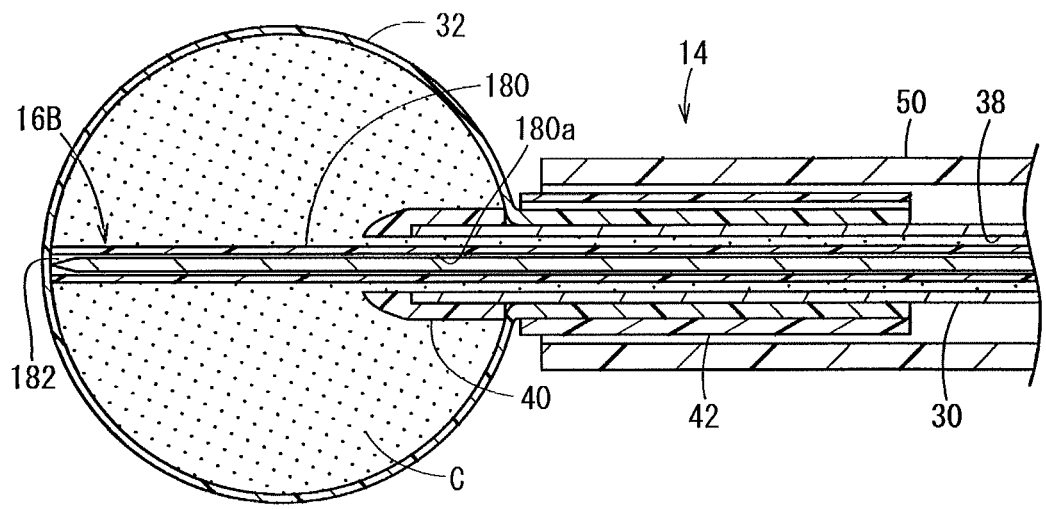
FIG. 13B is a side cross-sectional view illustrating a placement device according to a seventh modification example.

In a deployment operation device 16B according to a seventh modification example illustrated in FIG. 13B, a mandrel 180 is configured to include a tubular body having a penetrating path 180a along the axial direction. This mandrel 180 enables various effects to be obtained. For example, if the mandrel 180 is inserted before the filling of the bone filling material C, it is possible to discharge the air in the flow path 38 via the penetrating path 180a during the filling of the bone filling material C. In addition, if a needle member 182 is configured to be movably accommodated in the penetrating path 180a, it is possible to immediately break the filling balloon 32 by causing the needle member 182 to move forward after the bone filling material C is cured.

In addition, as another modification example of the bone treatment system 10, the grip portion 34 for operating the placement device 14 is not limited to the Y-connector. Various structures can be adopted instead. For example, it is possible to adopt a structure in which the grip portion is configured to serve as a hub formed of one port, and which includes a valve body having a capability of a piston which can elastically move forward and rearward inside the port. In this case, it is preferable to adopt a configuration in which the valve body is opened by being pushed to the distal side when the supply device 36 is connected to the port, and in which leakage of the bone filling material C is prevented by providing a connection port which is closed by being elastically restored in response to disconnection of the supply device 36. In this manner, the grip portion having one port can realize the supply of the bone filling material C from the supply device 36 and the insertion of the mandrel 70 or the needle member 80 after the supply.

Figure 14:
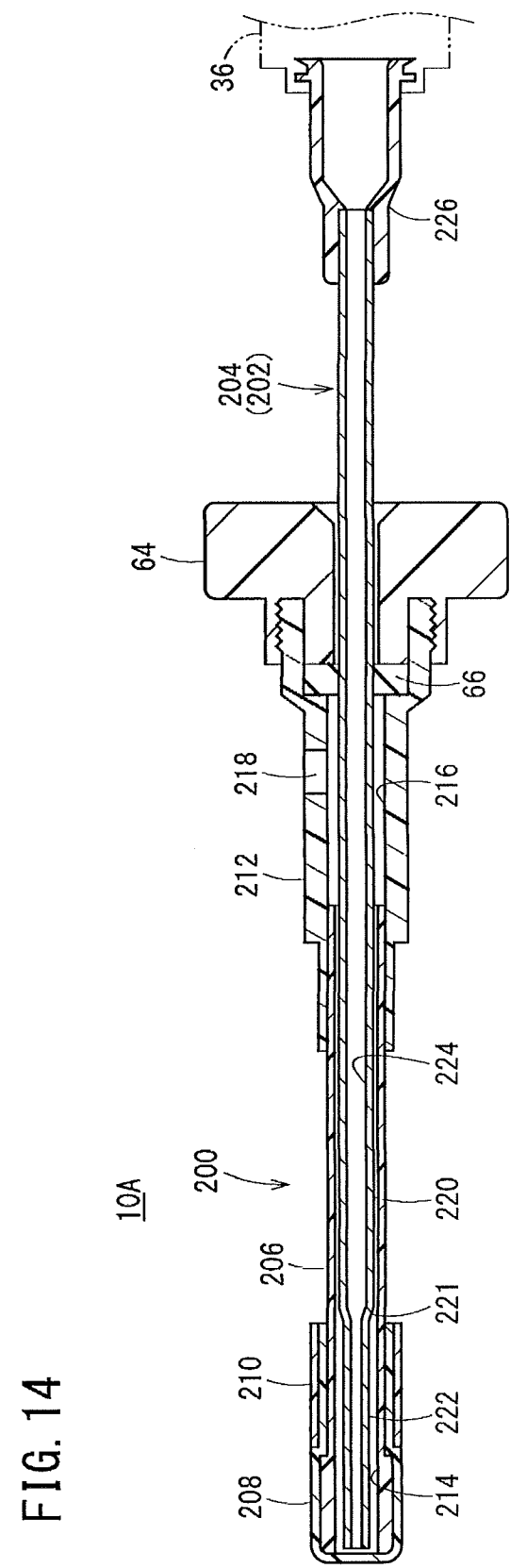
FIG. 14 is a side cross-sectional view of a placement device of a bone treatment system according to another embodiment.

A bone treatment system 10A according to another embodiment illustrated in FIG. 14 has a configuration in which a placement device 200 includes one port accommodating a mandrel 204 serving as a deployment operation device 202, and in which the bone filling material C is supplied via the mandrel 204. Though not illustrated, the bone treatment system 10A includes the space forming device 12 and the needle member 80 (deployment operation device 202), similar to the bone treatment system 10 illustrated in FIG. 1.

The placement device 200 includes a shaft 206, a filling balloon 208, a fixing tube 210, and a grip portion 212. The shaft 206 has a distal end portion possessing a relatively large diameter (large diameter portion) which supports the deflated filling balloon 208. A hollow portion 214 (lumen) is formed inside the shaft 206 and extends through the shaft 206 in the axial direction. The filling balloon 208 has a configuration which is the same as that of the filling balloon 32 illustrated in FIG. 1. The proximal end portion of the balloon 208 is fixed to the fixing tube 210, and the filling balloon 208 can be inflated in the distal end direction of the fixing tube 210.

The grip portion 212 includes an introduction space portion 216 possessing the inner diameter which can be fitted to (i.e., accommodate) the outer diameter of the shaft 206, and is fixedly attached to the proximal end portion of the shaft 206. A wall portion of the grip portion 212 which surrounds the introduction space portion 216 includes a communication hole 218 (gas discharge portion) which communicates the introduction space portion 216 with the outside and discharges the air internally present in a hollow portion 214 when the bone filling material C is supplied. In addition, similar to the grip portion 34 illustrated in FIG. 3, the guide member 64 and the valve body 66 are disposed on the proximal side of the grip portion 212.

This placement device 200 has a configuration from which the sheath 50 illustrated in FIG. 1 is omitted. However, the shaft 206 or the filling balloon 208 may be configured to be accommodated in the sheath, of course.

In contrast, the mandrel 204 possesses a tubular shape which can be inserted into or removed from the hollow portion 214. The mandrel 204 includes a tubular body portion 220 having a sufficient length which enables the proximal side of the mandrel 204 to protrude from the proximal end portion of the placement device 200, and a tubular distal end portion 222 which is connected to the distal side of the tubular body portion 220. The outer diameter of the tubular distal end portion 222 is less than the outer diameter of the tubular body portion 220. In addition, between the tubular body portion 220 and the tubular distal end portion 222, a tapered portion 221 whose outer and inner diameters gradually decrease in the distal end direction and connects both of these is formed.

A flow path 224 which penetrates (passes through) the mandrel 204 in the axial direction is disposed inside the mandrel 204. The flow path 224 is formed so that a distal end portion of the flow path is narrowed at the place where the outer diameter of the tubular body portion 220 is narrowed, namely at the tubular distal end portion 222. In addition, a hub 226 for connecting the supply device 36 which supplies the bone filling material C is disposed at the proximal end portion of the tubular body portion 220.

The bone treatment system 10A according to another embodiment is configured as described above. Hereinafter, an operation and an effect of this bone treatment system 10A will be described. Similar to the bone treatment system 10 illustrated in FIG. 1, the placement device 200 of the bone treatment system 10A is used iafter the space forming device 12 forms the space 108 inside the radius 100.

Figure 15A:
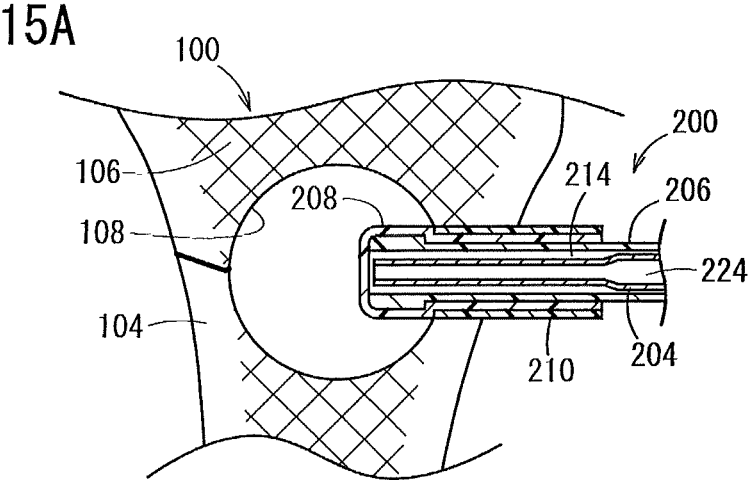
FIG. 15A is a first illustrating view for illustrating a placement measure of the bone filling material using the placement device in FIG. 14.

A surgeon performs a grip operation on the grip portion 212 of the placement device 200 in which the mandrel 204 is set, and as illustrated in FIG. 15A, the surgeon inserts the distal end portion of the placement device 200 into the space 108 of the radius 100. After the distal end portion (large diameter portion) of the shaft 206 is inserted into the space 108, the supply device 36 is connected to the hub 226 of the mandrel 204, and the paste-like bone filling material C1 is supplied to the flow path 224 of the mandrel 204.

Figure 15B:
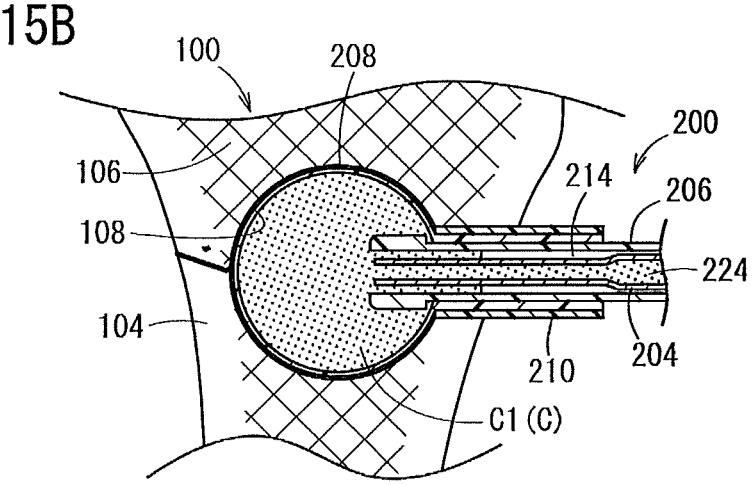
FIG. 15B is a second illustrating view for illustrating the placement measure of the bone filling material, subsequent to FIG. 15A.

As illustrated in FIG. 15B, the supplied bone filling material C1 flows from the distal end portion of the mandrel 204 via the flow path 224, further fills the filling balloon 208, and inflates the filling balloon 208. When the bone filling material C1 flows out from the mandrel 204, the air present in the shaft 206 or the filling balloon 208 flows in the proximal end direction through the hollow portion 214, and is discharged from the communication hole 218 of the grip portion 212. In this manner, the inside of the filling balloon 208 is smoothly filled with the bone filling material C1.

Figure 15C:
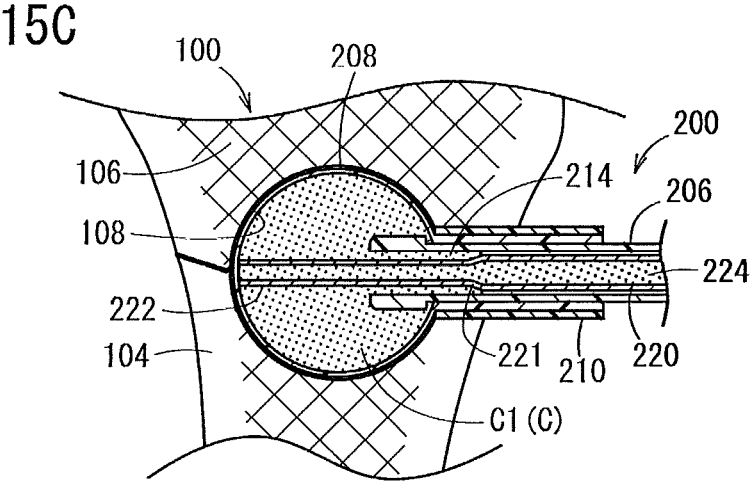
FIG. 15C is a third illustrating view for illustrating the placement measure of the bone filling material, subsequent to FIG. 15B.
Figure 16A:
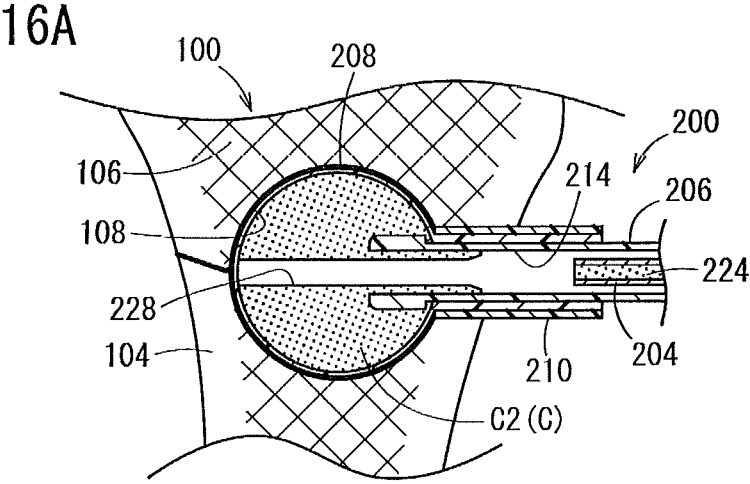
FIG. 16A is a fourth illustrating view for illustrating the placement measure of the bone filling material, subsequent to FIG. 15C.

After the filling of the bone filling material C1 (or during the filling), as illustrated in FIG. 15C, the surgeon operates the mandrel 204 to move the mandrel 204 forward, and causes the distal end portion of the mandrel 204 to come into contact with the inner surface of the inflated filling balloon 208 at the distal end portion of the filling balloon 208 (i.e., at the portion of the expanded filling balloon 208 diametrically opposite the placement device 200). Thereafter, the surgeon causes the bone filling material C to be cured for a predetermined waiting time, and then pulls out the mandrel 204 from the cured bone filling material C2. In this manner, as illustrated in FIG. 16A, a passage 228 is formed inside the cured bone filling material C2.

Figure 16B:
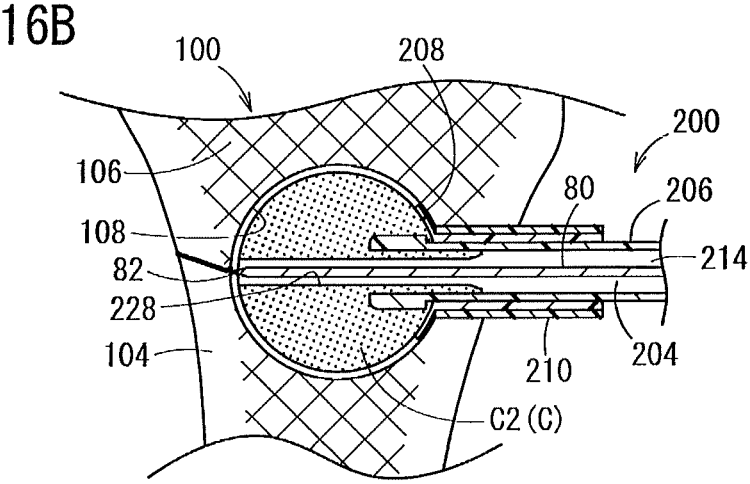
FIG. 16B is a fifth illustrating view for illustrating the placement measure of the bone filling material, subsequent to FIG. 16A.

As illustrated in FIG. 16B, the needle member 80 is then inserted into the passage 228 instead of the mandrel 204. The needle tip 82 of the needle member 80 moves forward toward and comes into contact with the distal end portion of the filling balloon 208 which the passage 228 opposes, thereby breaking the filling balloon 208 from the rear side of the space 108. In this case, the passage 228 is constructed so that the distal side of the passage 228 is narrow based on a shape of the mandrel 204, but is formed to be gradually narrowed by the tapered portion 221. Accordingly, the needle member 80 can be smoothly operated to move forward. The cured bone filling material C2 is exposed inside the space 108 by the filling balloon 208 being broken.

Figure 16C:
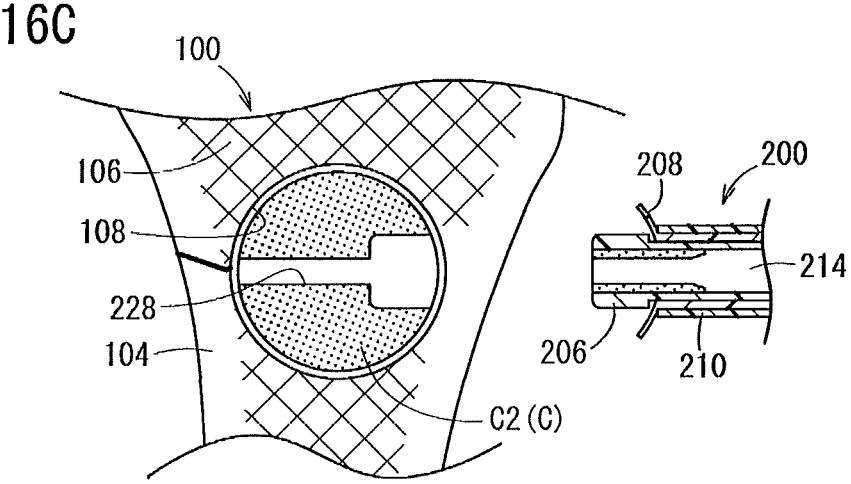
FIG. 16C is a sixth illustrating view for illustrating the placement measure of the bone filling material, subsequent to FIG. 16B.

After the bone filling material C is exposed, as illustrated in FIG. 16C, the needle member 80 is pulled out from the passage 228, and further the placement device 200 is pulled out from the inside of the radius 100. In this manner, the cured bone filling material C2 is placed in the space 108 of the radius 100.

As described above, the bone treatment system 10A according to another embodiment can also obtain an operation effect which is the same as that of the bone treatment system 10. In addition, in this bone treatment system 10A, it is possible to cause the paste-like bone filling material C1 to flow via the inside of the linear mandrel 204. Therefore, it is possible to smoothly fill the filling balloon 208 with the paste-like bone filling material C1.

Note that, a partial configuration (tip 40 and the like) of the bone treatment system 10 illustrated in FIG. 1 or the above-described modification examples illustrated in FIGS. 10A to 13B can also be applied to the bone treatment system 10A. In addition, the bone treatment system 10A can adopt various modification examples or application examples, of course. For example, the mandrel 204 may be formed in a shape having a uniform thickness in the axial direction. In addition, the mandrel 204 may adopt a configuration which has the hollow portion 214 through which the needle member 80 can pass, and in which the filling balloon 208 is broken via the hollow portion 214. In short, the placement device and the mandrel may be formed in a dual structure which enables relative movement in the axial direction, or the placement device, the mandrel, and the needle member may be formed in a triple structure which enables relative movement in the axial direction.

In the above-described embodiments, the filling balloon 32 is ruptured inside the bone after the bone filling material C is cured, that is, after the bone filling material C is in a state of being cured to such an extent so as not to be disintegrated by the body fluid. However, the filling balloon 32 may be ruptured before the bone filling material C is in the state of being cured to such an extent so as not to be disintegrated by the body fluid. According to this method, a higher therapeutic effect can also be obtained as compared to a case where the bone filling material C is introduced into the bone without using the balloon.

The detailed description above describes embodiments of a bone treatment system and method representing examples of the invention disclosed here. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A bone treatment system comprising:
a shaft possessing a lumen configured to permit a bone filling material to flow through the lumen and be delivered to a bone treatment site;
a balloon disposed on a distal end of the shaft configured to be filled with the bone filling material via the lumen; and
a deployment operation device insertable into the lumen and configured to break the balloon after the balloon is in an inflated state filled with the bone filling material to expose the bone filling material,
wherein the deployment operation device includes an insertion member which is insertable into the lumen and the balloon, and whose distal end portion is movable close to or into contact with an inner surface of the balloon in the inflated state.

2. The bone treatment system according to claim 1, wherein the balloon is made of an elastic material.

3. The bone treatment system according to claim 1, wherein the insertion member is positioned in the bone filling material when the insertion member is positioned in the balloon and is removed from the bone filling material to form a hollow portion in the filling material, wherein the deployment operation device further includes a needle member which is guided inside the hollow portion after the insertion member is pulled out from the bone filling material, and which breaks the balloon.

4. The bone treatment system according to claim 1, wherein the insertion member is positioned in the bone filling material when the insertion member is positioned in the balloon and is removed from the bone filling material to form a hollow portion in the filling material, wherein the deployment operation device causes a solution for dissolving the balloon to flow into the hollow portion, thereby breaking the balloon.

5. The bone treatment system according to claim 1, wherein the insertion member is a tubular body possessing a penetrating path in an axial direction, and
wherein the deployment operation device further includes a needle member which is inserted into the penetrating path and breaks the balloon.

6. The bone treatment system according to claim 1, wherein the balloon is configured so that in the inflated state, a thickness of a portion of the balloon which is contacted by a distal end portion of the insertion member is less than a thickness of the balloon in a vicinity of an attachment portion at which the balloon is attached to the shaft.

7. The bone treatment system according to claim 1, wherein the insertion member is positioned in the bone filling material when the insertion member is positioned in the balloon and is removed from the bone filling material after the bone filling material is cured to form a hollow portion in the filling material, wherein an outer peripheral surface of the insertion member is coated with lubricant to provide the insertion member with a lubricating property for facilitating removal of the insertion member from the cured bone filling material.

8. The bone treatment system according to claim 1, further comprising an imaging unit on the balloon which is configured to recognize the balloon during radiation photography.

9. A bone treatment system comprising:
a shaft possessing a distal end portion at which is held a balloon possessing an interior that is fillable with bone filling material, the balloon being inflatable in a distal direction of the shaft so that the inflated balloon extends distally beyond a distal-most end of the shaft, the distal end of the shaft including the balloon being configured to be positioned in a space spanning a fracture in a bone, the shaft including a lumen extending along the shaft, the lumen in the shaft communicating with both an injection port which is connectable to a bone filling material source and the interior of the balloon so that when the bone filling material source is connected to the injection port, bone filling material is conveyed along the lumen and introduced into the interior of the balloon while the balloon is positioned in the space spanning the fracture to fill the balloon and cause the balloon to inflate in the space;
an elongated mandrel configured to be introduced into the lumen while the balloon filled with the bone filling material is positioned in the space so that the elongated mandrel passes through the bone filling material, and to be removed from the bone filling material after curing of the bone filling material to produce a passage in the bone filling material that communicates with the balloon; and
a needle member configured to be introduced into the lumen after the elongated mandrel is removed and while the balloon filled with the cured bone filling material and provided with the passage is positioned in the space to move a tip end of the needle into contact with the balloon to break the balloon so that the balloon is removable from the space together with the shaft while the cured bone filling material remains in the space.

10. The bone treatment system according to claim 9, wherein the balloon is made of an elastic material.

11. The bone treatment system according to claim 9, wherein the balloon is made of a non-elastic material.

12. The bone treatment system according to claim 9, further comprising a fixing tube overlying the balloon and fixing the balloon to the distal end portion of the shaft.

13. The bone treatment system according to claim 12, wherein the fixing tube includes inner surface facing the balloon, the inner surface of the fixing tube including a plurality of circumferentially spaced apart grooves which receive portions of the balloon to create a plurality of circumferentially spaced apart air discharge paths for discharging air in the balloon to outside the shaft.

14. The bone treatment system according to claim 9, further comprising an imaging unit on the balloon configured to recognize the balloon during radiation photography.

15. A method of treating a fracture in a bone, the method comprising:
inserting a balloon disposed on a distal end of a shaft into a space in the bone, the space spanning the fracture in the bone, the balloon possessing an interior;
introducing bone filling material from a lumen of the shaft into the interior of the balloon to inflate the balloon in the space to and cause the balloon to contact the bone surrounding the space;
breaking the balloon using a deployment operation device inserted into the lumen of the shaft to expose the bone filling material in the space; and
removing the balloon from the space while the bone filling material remains in the space.

16. The method according to claim 15, further comprising curing the bone filling material after introducing the bone material into the balloon and before breaking the balloon.

17. The method according to claim 15, further comprising introducing an elongated mandrel of the deployment operation device into the bone filling material in the balloon before breaking the balloon, curing the bone filling material while the elongated mandrel is positioned in the bone filling material and removing the elongated mandrel from the cured bone filling material so that a passage exists in the bone filling material.

18. The method according to claim 17, wherein the breaking of the balloon comprises introducing a needle of the deployment operation device into the passage in the bone filling material and moving a tip of the needle into contact with the balloon.

19. The method according to claim 17, wherein the elongated mandrel is introduced into the bone filling material until a distal end of the elongated mandrel contacts an inner surface of the balloon.

* * * * *